US012209261B2

(12) United States Patent
Lee et al.

(10) Patent No.: US 12,209,261 B2
(45) Date of Patent: Jan. 28, 2025

(54) MEDIA FOR THE EXPRESSION OF RECOMBINANT VITAMIN K-DEPENDENT PROTEINS

(71) Applicant: CSL Behring Lengnau AG, Lengnau BE (CH)

(72) Inventors: Yih Yean Lee, Victoria (AU); Chee Kin Andrew Low, Victoria (AU); Campbell Douglas Aitken, Victoria (AU); Steven Patrick Byrne, Victoria (AU); Mark John Ferres Edwards, Victoria (AU)

(73) Assignee: CSL BEHRING LENGNAU AG, Lengnau Be (CH)

(*) Notice: Subject to any disclaimer, the term of this patent is extended or adjusted under 35 U.S.C. 154(b) by 153 days.

(21) Appl. No.: 15/780,344

(22) PCT Filed: Dec. 2, 2016

(86) PCT No.: PCT/EP2016/079585
§ 371 (c)(1),
(2) Date: May 31, 2018

(87) PCT Pub. No.: WO2017/093482
PCT Pub. Date: Jun. 8, 2017

(65) Prior Publication Data
US 2018/0362952 A1  Dec. 20, 2018

(30) Foreign Application Priority Data
Dec. 2, 2015  (EP) .................................. 15197516

(51) Int. Cl.
| | |
|---|---|
| *C12N 9/64* | (2006.01) |
| *C07K 14/47* | (2006.01) |
| *C07K 14/745* | (2006.01) |
| *C07K 14/76* | (2006.01) |
| *C12N 5/071* | (2010.01) |
| *C12N 5/16* | (2006.01) |
| *A61K 38/00* | (2006.01) |

(52) U.S. Cl.
CPC ........ *C12N 9/6437* (2013.01); *C07K 14/4702* (2013.01); *C07K 14/745* (2013.01); *C07K 14/76* (2013.01); *C12N 5/0682* (2013.01); *C12N 5/16* (2013.01); *A61K 38/00* (2013.01); *C07K 2319/31* (2013.01); *C12N 2500/30* (2013.01); *C12N 2500/44* (2013.01)

(58) Field of Classification Search
None
See application file for complete search history.

(56) References Cited

U.S. PATENT DOCUMENTS

| 4,784,950 A | 11/1988 | Hagen et al. |
|---|---|---|
| 8,785,194 B2 | 7/2014 | Gorfien et al. |
| 2007/0212770 A1 | 9/2007 | Grillberger et al. |
| 2018/0312811 A1* | 11/2018 | Tian ..................... C12N 5/0682 |

FOREIGN PATENT DOCUMENTS

| CA | 2623974 A1 * | 4/2007 | ........... C12N 5/0018 |
|---|---|---|---|
| EP | 1816201 A1 * | 8/2007 | ...... C12Y 304/21021 |
| WO | WO 2002/29045 A2 | 4/2002 | |
| WO | WO 2003/029442 | 4/2003 | |
| WO | WO 2004/024899 | 3/2004 | |
| WO | WO 2005/035748 | 4/2005 | |
| WO | WO 2006/089613 | 8/2006 | |
| WO | WO 2006/101474 A1 | 9/2006 | |
| WO | WO 2007/003640 A1 | 1/2007 | |
| WO | WO 2007/036291 A2 | 4/2007 | |
| WO | WO 2007/075976 A2 | 7/2007 | |
| WO | WO 2007/090584 A1 | 8/2007 | |
| WO | WO 2011/003153 A1 | 1/2011 | |
| WO | WO 2014/110433 A1 | 7/2014 | |

OTHER PUBLICATIONS

Suttie J. W. "Synthesis of Vitamin K-Dependent Proteins," The FASEB Journal, 1993, vol. 7, pp. 445-452.
Mollerup I., "The Use of RP-HPLC for Measuring Activation and Cleavage of rFVIIa During Purification," Biotechnology and Bioengineering, 1995, vol. 48, pp. 501-505.
Wong W.-Y. et al., "Clinical Efficacy and Recovery Levels of Recombinant FVIIa (NovoSeven) in the Treatment of Intracranial Haemorrhage in Severe Neonatal FVII Deficiency," Haemophilia, 2000, vol. 6, pp. 50-54.
Rost S. et al., "Mutations in VKORC1 Cause Warfarin Resistance and Multiple Coagulation Factor Deficiency Type 2," Nature, 2004, vol. 427, pp. 537-541.
Wajih N. et al., "Increased Production of Functional Recombinant Human Clotting Factor IX by Baby Hamster Kidney Cells Engineered to Overexpress VKORC1, the Vitamin K 2,3-Epoxide-Reducing Enzyme of the Vitamin K Cycle," The Journal of Biological Chemistry, 2005, vol. 280, No. 36, pp. 31603-31607.
Nilsang S. et al., "Effect of α-Ketoglutarate on Monoclonal Antibody Production of Hybridoma Cell Lines in Serum-Free and Serum-Containing Medium," Applied Biochemistry and Biotechnology, 2008, vol. 151, pp. 589-501.
Kim T. K., "Mammalian Cell Transfection: The Present and the Future," Anal Bioanal Chemistry, 2010, vol. 397, pp. 3173-3178.
Van Geffen M. et al., "Pharmacodynamics of Recombinant Activated Factor VII and Plasma-Derived Factor VII in a Cohort of Severe FVII Deficient Patients," Thrombosis Research, 2013, vol. 132, pp. 116-122.
International search report and the written opinion of the international search authority, issued in corresponding International Patent Application No. PCT/EP2016/079585, mailed Jan. 30, 2017, 14 pages.

(Continued)

*Primary Examiner* — Emily A Cordas
(74) *Attorney, Agent, or Firm* — Finnegan, Henderson, Farabow, Garrett & Dunner, LLP

(57) ABSTRACT

The present invention relates to a method for increasing the activity and/or the yield of a recombinant vitamin K-dependent protein expressed in cell culture. The present invention further relates to uses and compositions of matter.

11 Claims, 24 Drawing Sheets

(56) References Cited

OTHER PUBLICATIONS

The extended European search report, issued in corresponding European Patent Application No. 15197516.6, mailed Apr. 8, 2016, 12 pages.

Chromogenix Coaset FVII product information, 1 page.

Vatandoost et al., "Expression of Biologically Active Human Clotting Factor IX in *Drosophila* S2 Cells: y-Carboxylation of a Human Vitamin K-Dependent Protein by the Insect Enzyme," Biotechnology Progress, vol. 28, No. 1, pp. 45-51 (2012).

Lee et al., "Metabolism of Vitamin K and Vitamin K 2,3-Epoxide via Interaction with a Common Disulfide," Biochemistry, vol. 23, No. 10, pp. 2246-2252 (1984).

Soute et al., "Stimulation of the Dithiol-dependent Reductases in the Vitamin K Cycle by the Thioredoxin System," Biochem. J., vol. 281, pp. 255-259 (1992).

Wallin et al., "Warfarin Poisoning and Vitamin K Antagonism in Rat and Human Liver," Biochem. J., vol. 241, pp. 389-396 (1987).

Schneider's Insect Medium, Sigma-Aldrich, 2 pages (2014).

Berg et al., "The Citric Acid Cycle Oxidizes Two-Carbon Units," Biochemistry, 5$^{th}$ edition, New York: W H Freeman, 12 pages (2002).

Derouazi et al., "Genetic characterization of CHO production host DG44 and derivative recombinant cell lines," Biochem Biophys Res Commun, 2006, 340(4):1069-1077.

Yun et al., "Effect of antioxidants on the apoptosis of CHO cells and production of tissue plasminogen activator in suspension culture," J Biosci Bioeng, 2001, 91(6):581-585.

Yun et al., "Combined addition of glutathione and iron chelators for decrease of intracellular level of reactive oxygen species and death of Chinese hamster ovary cells," J Biosci Bioeng, 2003, 95(2):124-127.

Bates et al., "The Kinetics and Mechanism of Iron (III) Exchange Between Chelates and Transferrin," J Biol Chem, Jun. 25, 1967;242(12):2810-2815.

Jordan et al., "The Mammalian Transferrin-Independent Iron Transport System May Involve a Surface Ferrireductase Activity," Biochem J, Sep. 15, 1994;302:875-879.

Trinder et al, "Mechanisms of Ferric Citrate Uptake by Human Hepatoma Cells," Am J Physiol. 275 (Gastrointest. Liver Physiol. 38): 38:G279-G286 (Aug. 1998).

Mjayasankaran et al., "Animal Cell Culture Media," Encyclopedia of Industrial Biotechnology:Bioprocess, Bioseparation, and Cell Technology, Apr. 15, 2010, 15 pages.

\* cited by examiner

MEDIA FOR THE EXPRESSION OF RECOMBINANT VITAMIN K-DEPENDENT PROTEINS

This application is the United States national stage entry under 35 U.S.C. § 371 of International Application No. PCT/EP2016/079585, filed on Dec. 2, 2016 and published as WO 2017/093482 A1, which claims priority to European Patent Application No. 15197516.6, filed on Dec. 2, 2015. The contents of these applications are each incorporated herein by reference in their entirety.

FIELD OF THE INVENTION

The present invention relates to a method for increasing the activity and/or the yield of a recombinant vitamin K-dependent protein expressed in cell culture. The present invention further relates to uses and compositions of matter.

BACKGROUND OF THE INVENTION

Vitamin K is involved in the carboxylation of certain glutamic acid residues in proteins to form gamma-carboxyglutamate residues (Gla-residues). The modified residues are located within specific protein domains called Gla domains. Gla-residues are usually involved in calcium binding. The Gla-residues are essential for the biological activity of all known Gla-proteins.

The biochemistry of how vitamin K is used to convert Glu to Gla has been elucidated over the past thirty years. Within the cell, vitamin K undergoes electron reduction to a reduced form of vitamin K (called vitamin K hydroquinone) by the enzyme vitamin K epoxide reductase (VKOR). The gene encoding VKOR (VKORC1) is described in detail in Rost et al, 2004 ((2004) Nature, 427, 537-541)). Another enzyme then oxidizes vitamin K hydroquinone to allow carboxylation of Glu to Gla; this enzyme is called the gamma-glutamyl carboxylase or the vitamin K-dependent carboxylase (VKGC). The carboxylation reaction will only proceed if the carboxylase enzyme is able to oxidize vitamin K hydroquinone to vitamin K epoxide at the same time; the carboxylation and epoxidation reactions are said to be coupled reactions. Vitamin K epoxide is then re-converted to vitamin K by the vitamin K epoxide reductase. These two enzymes comprise the so-called vitamin K cycle.

At present, the following human Gla-containing proteins have been characterized to the level of primary structure: the blood coagulation factors II (prothrombin), VII, IX, and X, the anticoagulant proteins C and S, and the Factor X-targeting protein Z as well as the bone Gla-protein osteocalcin, the calcification inhibiting matrix Gla protein (MGP), the cell growth regulating growth arrest specific gene 6 protein (Gas6), and the four transmembrane Gla proteins (TMGPs) of yet unknown function. Gas6 can function as a growth factor that activates the Axl receptor tyrosine kinase and stimulates cell proliferation or prevents apoptosis in some cells. In all cases in which their function was known, the presence of the Gla-residues in these proteins turned out to be essential for functional activity. The multiple Gla residues allow the Gla-domain to undergo conformational changes which are required for the activity of vitamin K-dependent proteins in combination with binding to phospholipid membrane surfaces.

The vitamin K-dependent blood coagulation proteins require full or nearly full carboxylation to bind to membrane surfaces in the presence of calcium ions. If vitamin K antagonists inhibit gamma carboxylation, thus undercarboxylated vitamin K-dependent proteins cannot form the calcium dependent structure which results in low affinity to phospholipids membranes and less activity. Missing procoagulant activity of undercarboxylated Factor IX mutants found in hemophilia B patients can be assigned to impaired calcium-induced conformational changes and loss in the ability to bind phospholipid vesicles.

Methods for expressing vitamin K-dependent proteins have been disclosed in the prior art. WO 2011/003153 discloses a process for the fermentation of eukaryotic cells expressing one or more vitamin K-dependent proteins wherein one or more compounds selected from a list comprising i) reduced forms of vitamin K and/or ii) reduced forms of a vitamin K analog and/or iii) reduced forms of a vitamin K precursor are added to the cell culture medium before and/or during the fermentation process. WO 2006/101474 discloses methods of increasing the amount of carboxylated vitamin K-dependent protein in a cell, comprising introducing into a cell that expresses a first nucleic acid encoding a vitamin K-dependent protein a second heterologous nucleic acid encoding vitamin K epoxide reductase (VKOR) under conditions whereby said first and second nucleic acids are expressed to produce a vitamin K-dependent protein and VKOR, respectively. WO 2007/075976 discloses methods for producing biologically active vitamin K-dependent proteins, particularly Factor IX. The method aims at producing Factor IX at a level of at least about 15 mg/L and that is at least 25% biologically active. The method relies upon co-expression of one or more of paired basic amino acid converting enzyme (PACE), vitamin K-dependent epoxide reductase (VKOR) and vitamin K-dependent gamma-glutamyl carboxylase (VKGC) at a preferred ratio so that the vitamin K-dependent protein is efficiently produced and processed by a recombinant cell.

Cell culture media comprising TCA intermediates such as alpha-ketoglutaric acid have been applied for antibody expression (WO 2007/036291 and Nilsang et al., 2008, Appl Biochem Biotechnol, 151:489-501).

Vitamin K-dependent proteins are used in the treatment of a variety of bleeding disorders. For therapeutic uses, recombinant protein products are advantageous over plasma-derived protein, since plasma-derived protein has a potentially higher risk of pathogen contamination and it is associated with high efforts and expense as its process of preparation is dependent on human plasma donors. A strong need exists for enhancing the recombinant expression of vitamin K-dependent proteins in host organisms resulting in increased protein yield. Further, there is a need to prepare vitamin K-dependent proteins with enhanced protein activity. The method according to the present invention fulfills this unmet need in the art.

SUMMARY OF THE INVENTION

The present invention relates to a method for increasing the yield of a recombinant vitamin K-dependent protein. The method of the present invention is also for enhancing the activity of a recombinant vitamin K-dependent protein.

It has been surprisingly found that supplementing a cell culture expressing a recombinant vitamin K-dependent protein with L-glutathione or a TCA intermediate significantly increases the yield and/or the biological activity of the recombinant vitamin K-dependent protein.

In one embodiment, the present invention provides a method for increasing the yield of a recombinant vitamin K-dependent protein comprising the following steps:

a) providing host cells comprising an expression system expressing the recombinant vitamin K-dependent protein,
b) culturing the cells in a cell culture medium comprising one or more cell culture enhancing reagent(s), and
c) separating and/or isolating and/or purifying the recombinant vitamin K-dependent protein from the cell culture, wherein the one or more cell culture enhancing reagent(s) is/are selected from the group consisting of L-glutathione and TCA cycle intermediates.

In another embodiment, the present invention provides a method for enhancing the activity of a recombinant vitamin K-dependent protein comprising the following steps:
a) providing host cells comprising an expression system expressing the recombinant vitamin K-dependent protein,
b) culturing the cells in a cell culture medium comprising one or more cell culture enhancing reagent(s), and
c) separating and/or isolating and/or purifying the recombinant vitamin K-dependent protein from the cell culture, wherein the one or more cell culture enhancing reagent(s) is/are selected from the group consisting of L-glutathione and TCA cycle intermediates.

In a further embodiment, the invention relates to a method for increasing the yield of a recombinant vitamin K-dependent protein and for enhancing the activity of a recombinant vitamin K-dependent protein comprising the following steps:
a) providing host cells comprising an expression system expressing the recombinant vitamin K-dependent protein,
b) culturing the cells in a cell culture medium comprising one or more cell culture enhancing reagent(s), and
c) separating and/or isolating and/or purifying the recombinant vitamin K-dependent protein from the cell culture, wherein the one or more cell culture enhancing reagent(s) is/are selected from the group consisting of L-glutathione and TCA cycle intermediates.

In one embodiment, the TCA cycle intermediates are selected from alpha-ketoglutaric acid, succinic acid, oxaloacetic acid, malic acid, fumaric acid and citric acid. The one or more cell culture enhancing reagent(s) are preferably present in an amount effective for increasing the yield of the recombinant vitamin K-dependent protein and/or for enhancing the activity of the recombinant vitamin K-dependent protein.

In one embodiment, L-glutathione is provided at a concentration of 0.5-13 mmol/L, preferably 2-10 mmol/L, more preferably 3.75-7.5 mmol/L in the cell culture. In one embodiment, alpha-ketoglutaric acid is provided at a concentration of 5-50 mmol/L, preferably 10-40 mmol/L, more preferably 15-30 mmol/L in the cell culture. In one embodiment, succinic acid is provided at a concentration of 2-50 mmol/L, preferably 5-30 mmol/L, more preferably 7.5-15 mmol/L in the cell culture. In one embodiment, oxaloacetic acid is provided at a concentration of 5-50 mmol/L, preferably 10-40 mmol/L, more preferably 15-30 mmol/L in the cell culture. In one embodiment, malic acid is provided at a concentration of 5-50 mmol/L, preferably 7.5-30 mmol/L, more preferably 10-20 mmol/L in the cell culture. In one embodiment, fumaric acid is provided at a concentration of 2-50 mmol/L, preferably 5-30 mmol/L, more preferably 7.5-15 mmol/L in the cell culture. In one embodiment, citric acid is provided at a concentration of 0.5-20 mmol/L, preferably 1-15 mmol/L, more preferably 1.5-3.75 mmol/L in the cell culture.

In one embodiment, the cell culture is a batch culture. In a further embodiment, the cell culture is a fed-batch culture. The cell culture enhancing reagent(s) may be present in the basal cell culture medium and/or in the feed medium. In a further embodiment, the cell culture is a perfusion culture. The cell culture enhancing reagent(s) may be present in the basal cell culture medium and/or in the perfusion medium.

In a preferred embodiment, the host cells are CHO cells.

In one embodiment, the recombinant vitamin K-dependent protein is selected from FIX, FVII, FX, FII, Protein C, Protein S, Protein Z, osteocalcin, the calcification inhibiting matrix Gla protein (MGP) and the cell growth regulating growth arrest specific protein 6 (Gas6). In a preferred embodiment, the vitamin K-dependent protein is FVII. In a most preferred embodiment, the vitamin K-dependent protein is a FVII albumin fusion protein.

Further provided is the use of L-glutathione, alpha-ketoglutaric acid, succinic acid, oxaloacetic acid, malic acid, fumaric acid and/or citric acid or salts thereof for increasing the yield of a recombinant vitamin K-dependent protein and/or for enhancing the activity of a recombinant vitamin K-dependent protein.

Also provided is the use of a cell culture medium comprising L-glutathione, alpha-ketoglutaric acid, succinic acid, oxaloacetic acid, malic acid, fumaric acid and/or citric acid for increasing the yield of a recombinant vitamin K-dependent protein and/or for enhancing the activity of a recombinant vitamin K-dependent protein.

Additionally, provided is a composition of matter, a bioreactor comprising the composition of matter, recombinant FVII prepared by the method of the invention, pharmaceutical compositions and medical uses.

DETAILED DESCRIPTION OF THE INVENTION

Figure 1A:
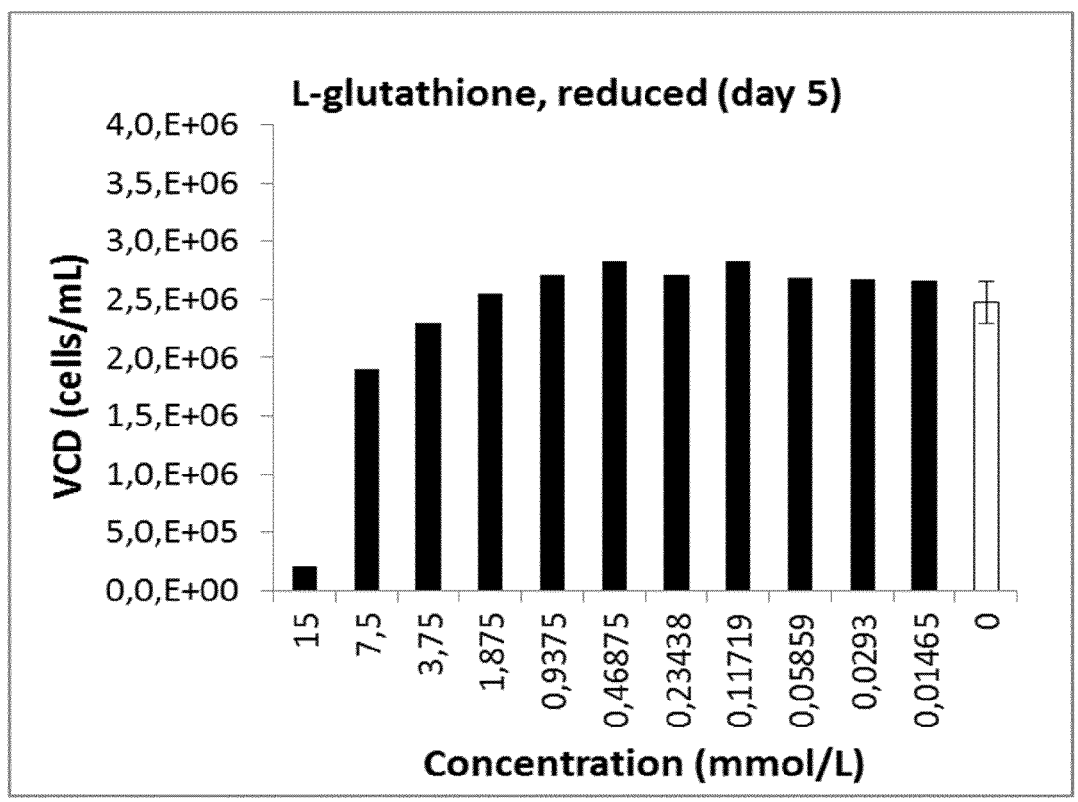
FIG. 1A: Viable cell density (VCD) of CHO cells expressing FVII that are grown in the presence of different concentrations of reduced L-glutathione for 5 or 7 days, respectively.
Figure 1A:
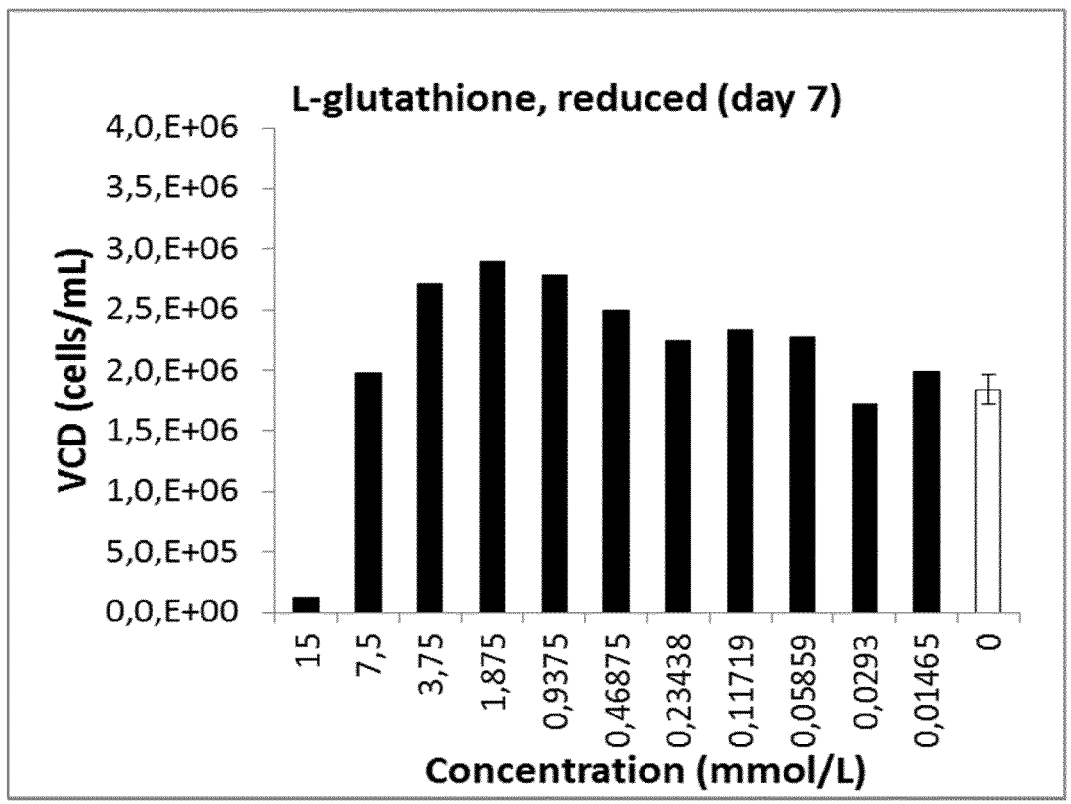

The term "vitamin K-dependent protein" as used herein relates to a protein requiring vitamin K for formation of γ-carboxyglutamate (Gla) residues. Such proteins can be characterized, for example, by the presence of one or more vitamin K-dependent carboxylation/γ-carboxyglutamic (Gla) domains. The glutamate residues in the Gla domain(s) are post-translationally modified by vitamin K-dependent carboxylation to form γ-carboxyglutamate (Gla) residues. This modification allows the Gla-domain(s) to undergo conformational changes that can be important for both, enzymatic activity and substrate binding, including, for instance, high-affinity binding to calcium ions and sometimes binding to phospholipid membrane surfaces. Non-limiting examples of vitamin K-dependent proteins include FIX, FVII, FX, FII, Protein C, Protein S, Protein Z, osteocalcin, the calcification inhibiting matrix Gla protein (MGP) and the cell growth regulating growth arrest specific protein 6 (Gas6).

The term "Factor VII" or "FVII" as used herein encompasses wild-type Factor VII and its activated form Factor VIIa, and variants of Factor VII and Factor VIIa that exhibit substantially the same or improved biological activity relative to wild-type Factor VII or Factor VIIa. The term "Factor VII" is thus intended to encompass Factor VII polypeptides in their uncleaved (zymogen) form, as well as those that have been proteolytically processed to yield their respective bioactive forms, which may be designated Factor VIIa. Typically, FVII is converted to its active form Factor VIIa (FVIIa) by proteolysis of the single peptide bond at Arg152-Ile153 leading to the formation of two polypeptide chains, a N-terminal light chain (24 kDa) and a C-terminal heavy chain (28 kDa), which are held together by one disulfide bridge. In contrast to other vitamin-K-dependent coagulation factors, no activation peptide, which is cleaved off during activation of these other vitamin-K dependent coagulation factors, has been described for FVII. The Arg152-Ile153 cleavage site and some amino acids downstream show homology to the activation cleavage site of other vitamin-K-dependent polypeptides. Essential for attaining the active conformation of Factor VIIa is the formation of a salt bridge after activation cleavage between Ile153 and Asp343. Activation cleavage of Factor VII can be achieved in vitro by Factor Xa, Factor XIIa, Factor IXa, Factor VIIa, Factor Seven Activating Protease (FSAP) and thrombin. Mollerup et al., 1995 (Biotechnol. Bioeng. 48:501-505) reported that some cleavage also occurs in the heavy chain at Arg290 and or Arg315.

Also encompassed is recombinant Factor VII, or variants thereof, for example, in which one or more amino acid deletions, additions, and/or substitutions have been introduced to modulate (e.g., increase, decrease) at least one biological activity of the protein. Unless otherwise specified, the FVII referred to herein may be unmodified or may exhibit post-translational modifications. Further encompassed are FVII fusion proteins, such as a FVII-albumin fusion. FVII may be human FVII. Also included are Factor VII proteins or FVII-related proteins from other organisms, such as other mammals.

FVII plays an important role in promoting blood coagulation. The current model of coagulation states that the physiological trigger of coagulation is the formation of a complex between tissue Factor (TF) and FVII on the surface of TF expressing cells, which are normally located outside the vasculature. This leads to the activation of Factor IX and Factor X ultimately generating some thrombin. In a positive feedback loop thrombin activates Factor VIII and Factor IX, the so-called "intrinsic" arm of the blood coagulation cascade, thus amplifying the generation of Factor Xa, which is necessary for the generation of the full thrombin burst to achieve complete hemostasis. It was shown that by administering supraphysiological concentrations of Factor VIIa hemostasis is achieved bypassing the need for Factor VIIIa and Factor IXa. The cloning of the cDNA for Factor VII (U.S. Pat. No. 4,784,950) made it possible to develop activated Factor VII as a pharmaceutical. Factor VIIa was successfully administered for the first time in 1988.

FVII is used in the treatment of hemophilia A and B in patients who developed inhibitors against replacement factors. Hemophilia A and B are inherited coagulation disorders. They result from a chromosome X-linked deficiency of blood coagulation Factor VIII (Hemophilia A) or from a chromosome X-linked deficiency of blood coagulation Factor IX (Hemophilia B) and affect almost exclusively males with an incidence between one and two individuals per 10,000. The X-chromosome defect is transmitted by female carriers who are not themselves clinically symptomatic. The clinical manifestation of hemophilia A and B is an increased bleeding tendency. The goal of therapy for hemophilia is to treat or prevent hemorrhage, thereby reducing disabling joint and tissue damage, and improving quality of life. In both, hemophilia A and in hemophilia B, the most serious medical problem in treating the disease is the generation of inhibitory alloantibodies against the replacement factors. Up to 30% of all hemophilia A patients develop inhibitory antibodies to Factor VIII. Inhibitory antibodies to Factor IX occur to a lesser extent but with more severe consequences, as they are less susceptible to immune tolerance induction therapy and have a higher potential to trigger allergic reactions when binding to Factor IX. The treatment for patients with hemophilia A (FVIII deficiency) or hemophilia B (Factor IX deficiency) who have developed inhibitory antibodies (Congenital Hemophilia with Inhibitors, CHwI) to FVIII or Factor IX (especially high titer inhibitors) is challenging, since normal replacement with Factor VIII or IX is not effective.

FVII can also be used as therapy to treat bleeding associated with perioperative and traumatic blood loss in subjects with normal coagulation systems. For example, FVII can be administered to a patient to promote coagulation and reduce blood loss associated with trauma and surgery and, further, reduce the requirement for blood transfusion. FVII can further be used in the treatment of acquired hemophilia, congenital FVII deficiency and Glanzmann's thrombasthenia.

The term "Factor IX" as used herein encompasses wild-type Factor IX and variants of Factor IX and IXa that exhibit substantially the same or improved biological activity relative to wild-type Factor IX or IXa. The term Factor IX is thus intended to encompass Factor IX polypeptides in their uncleaved (zymogen) form, as well as those that have been proteolytically processed to yield their respective bioactive forms, which may be designated Factor IXa.

Certain embodiments may include the recombinant production of wild-type Factor IX or Factor IXa, or variants thereof, for example, in which one or more amino acid deletions, additions, and/or substitutions have been introduced to modulate (e.g., increase, decrease) at least one biological activity of the protein. Factor IX may be human Factor IX. However, also included are Factor IX-related sequences from other organisms, such as other mammals known in the art.

The term "Factor X" as used herein encompasses wild-type Factor X and Xa, and variants of Factor X and Xa that exhibit substantially the same or improved biological activity relative to wild-type Factor X or Xa. The term Factor X is thus intended to encompass Factor X polypeptides in their uncleaved (zymogen) form, as well as those that have been proteolytically processed to yield their respective bioactive forms, which may be designated Factor Xa.

Certain embodiments may include the recombinant production of wild-type Factor X or Factor Xa, or variants thereof, for example, in which one or more amino acid deletions, additions, and/or substitutions have been introduced to modulate (e.g., increase, decrease) at least one biological activity of the protein. Factor X may be human Factor X. However, also included are Factor X-related sequences from other organisms, such as other mammals known in the art.

In other embodiments, the vitamin K-dependent protein product is Factor II, Protein C, Protein S, Protein Z, osteocalcin, the calcification inhibiting matrix Gla protein (MGP) and the cell growth regulating growth arrest specific protein 6 (Gas6).

The term "albumin" as used herein, includes polypeptides of the albumin family of proteins such as human serum albumin, including variants and derivatives thereof, such as genetically engineered or chemically modified albumin variants and fragments of albumin proteins. Human serum albumin (HSA, or HA), is a protein of 585 amino acids in its mature form, and is responsible for a significant proportion of the osmotic pressure of serum and also functions as a carrier of endogenous and exogenous ligands. Among other benefits, fusion to HSA or a fragment or variant thereof can increase the shelf-life, serum half-life, and/or therapeutic activity of its fusion partner. Albumin may be fused to its fusion partner on the N-terminus and/or on the C-terminus. The albumin portion of a fusion protein may also be derived from any vertebrate, especially any mammal. The albumin portion of the albumin-fusion protein may be from a different animal than the other protein portion of the fusion protein.

The term "cell culture enhancing reagent" as used herein relates to any one of L-glutathione and TCA intermediates.

The term "L-glutathione" (GSH; IUPAC name: (2S)-2-amino-5-[[(2R)-1-(carboxymethylamino)-1-oxo-3-sulfanyl-propan-2-yl]amino]-5-oxopentanoic acid) as used herein refers to a tripeptide with a gamma peptide linkage between the carboxyl group of the glutamate side-chain and the amine group of cysteine which is attached by normal peptide linkage to a glycine (γ-Glu-Cys-Gly). "L-glutathione" as used herein refers to reduced L-glutathione.

The term "TCA intermediates" or "tricaboxylic acid cycle intermediates" as used herein includes α-ketoglutaric acid (alpha-ketoglutaric acid), succinic acid, oxaloacetic acid, malic acid, fumaric acid and citric acid. The term TCA intermediate also refers to isocitric acid and succinyl-coenzyme A (succinyl-CoA).

The term "alpha-ketoglutaric acid" as used herein refers to alpha-ketoglutaric acid or salts thereof. The term "succinic acid" as used herein refers to succinic acid or salts thereof. The term "oxaloacetic acid" as used herein refers to oxaloacetic acid or salts thereof. The term "malic acid" as used herein refers to malic acid or salts thereof. The term "fumaric acid" as used herein refers to fumaric acid or salts thereof. The term "citric acid" as used herein refers to citric acid or salts thereof.

As used herein, "chromogenic activity" refers to the activity of a vitamin K-dependent protein in an assay measuring the enzymatic activity of the vitamin K-dependent protein by hydrolysis of a substrate resulting in a chromogenic product. Such assays are commercially available from e.g. Chromogenix.

The term "host cells" as used herein refers to cells from any cell line suitable for protein expression. The cell line may be of mammalian origin. Non-limiting examples of suitable mammalian cell lines are HEK 293 cells (human embryonic kidney 293 cells), BHK cells (baby hamster kidney cells), COS-1 cells, 3T3 cells, CHO cells (Chinese hamster ovary cells), hybridoma cells, NS0 mouse myeloma cells, NS1 mouse myeloma cells, Sp2/0 mouse myeloma cells, PER.C6 human retinoblastoma cells, Vero African Green Monkey Kidney cells and MDCK cells (Mardin-Darby Canine Kidney cells).

The term "cell culture medium" as used herein is a medium to culture mammalian cells comprising a minimum of essential nutrients and components required for cell growth such as vitamins, trace elements, salts, amino acids, carbohydrates in a preferably buffered medium. Non-limiting examples for such a cell culture medium are commercially available media and proprietary media. The cell culture medium can be a basal cell culture medium. The cell culture medium can also be a basal cell culture medium to which the feed medium or other additives have been added.

The term "basal medium" as used herein is a cell culture medium to culture mammalian cells. It refers to the medium in which the cells are cultured from the start of a cell culture. It is not used as an additive to another medium, however various components may be added to the medium. To the basal medium optionally further additives, feed medium or perfusion medium may be added during cell culture. The basal cell culture medium provides generally nutrients required for cell growth such as carbon sources, amino acids, vitamins and glucose.

The term "feed medium" as used herein relates to a concentrated nutrient formulation used as a feed in a cell culture. Feed medium is added to a cell culture during culturing cells. It is provided as a concentrated formulation to avoid dilution of the cell culture medium. The feeding rate varies depending on the process. The feeding rate is to be understood as an average feeding rate over the feeding period. A feed medium usually has higher concentrations of the components that are to be replenished than the basal medium. The feed medium replenishes components that are consumed during cell culture, such as amino acids and carbohydrates. The feed may be added in different modes such as continuous or periodically. The feed medium may be added daily, but may also be added more frequently, such as twice daily or less frequently, such as every second day.

The term "perfusion medium" as used herein relates to a medium suitable to replace cell culture medium that has been removed from a cell culture during culturing cells. Perfusion medium may have a similar or identical formulation as the basal medium. However, in the perfusion medium, several components may be present in higher or lower concentration or even be absent in comparison to the basal medium. The perfusion medium may also comprise components that are not present in the basal medium.

The cell culture medium, the basal medium, the feed medium and/or the perfusion medium may be serum-free, chemically defined, free of any proteins from human or animal origin and/or protein-free.

A "serum-free medium" as used herein refers to a cell culture medium for in vitro cell culture, which does not contain serum from animal origin. This is preferred as serum may contain contaminants or pathogens from said animal. Further, serum lacks a clear definition and may vary in its composition from batch to batch.

A "chemically defined medium" as used herein refers to a cell culture medium for in vitro cell culture, in which all components are known. More specifically, it does not contain any undefined supplements such as animal serum or plant hydrolysates. It may however comprise hydrolysates if all components have been analyzed and the exact composition of the hydrolysate is known.

A medium "free of proteins from animal or human origin" as used herein refers to a cell culture medium that does not contain any protein components from an animal or human source. However, such medium may comprise recombinant proteins derived from e.g., expression cell culture or bacterial expression.

A "protein-free medium" as used herein refers to a cell culture medium for in vitro cell culture comprising no proteins, except for proteins produced by the cell to be cultured, wherein protein refers to polypeptides of any length, but excludes single amino acids, dipeptides or tripeptides.

The term "cell culture" or "cultivation" includes cell cultivation and fermentation processes in all scales (e.g. from micro titer plates to large-scale bioreactors, i.e. from sub mL-scale to >1000 L scale), in all different process modes (e.g. batch, fed-batch, perfusion), in all process control modes (e.g. non-controlled, fully automated and controlled systems with control of e.g. pH, temperature, oxygen content), in all kind of fermentation systems (e.g. single-use systems, stainless steel systems, glass ware systems). Cell culture occurs at conditions (temperature, oxygen supply etc.) that are established for the respective cell lines used. The cells may be agitated or shaken to increase oxygenation and/or dispersion of nutrients during cultivation.

The term "fed-batch" as used herein relates to a cell culture in which the cells are fed continuously or periodically with a feed medium containing nutrients. The feeding may start shortly after starting the cell culture on day 0 or more typically one, two or three days after starting the culture. Feeding may follow a given schedule, such as every day, every two days, etc. Alternatively, the culture may be monitored for cell growth, nutrients or toxic by-products and feeding may be adjusted accordingly. In general, the following parameters are often determined on a daily basis and cover the viable cell concentration, product concentration and metabolites such as glucose, galactose, pH, osmolarity (a measure for salt content) and ammonium (growth inhibitor that negatively affects the growth rate). Compared to batch cultures (where no feeding occurs), higher product titers can be achieved in the fed-batch mode. Typically, a fed-batch culture is stopped at some point and the cells and/or the protein of interest in the medium are harvested.

The term "perfusion culture" as used herein refers to a cell culture in which perfusion medium is added continuously or semi-continuously during cell culture. The addition may start shortly after starting the cell culture on day 0 or one or more days after starting the culture. A portion of the cells, the cell culture medium and/or components in the medium are harvested continuously or semi-continuously during cell culture. Harvesting may start when the perfusion medium addition starts. The harvested components (e.g. proteins) may optionally be purified. The amount of perfusion medium added to a cell culture usually depends on the amount of cell culture medium removed from the culture during harvesting. The culture may be monitored for cell growth, nutrients or toxic by-products and the perfusion rate (amount of perfusion medium added over time) may be adjusted accordingly.

Methods for introducing DNA encoding a vitamin K-dependent protein into a host cell in order to achieve expression of the vitamin K-dependent protein are known from the prior art (e.g., Kim et al., Anal Bioanal Chem (2010), 379:3173-3178). The DNA encoding the vitamin K-dependent protein may further encode regulatory elements. Suitable elements should be selected based on the host cell. Preferred methods of transfection include the Lipofectamine® method, calcium phosphate precipitation and electroporation. The present invention can be carried out with transiently transfected or stably transfected host cells. In a preferred embodiment, the host cells are stably transfected with DNA encoding the vitamin K-dependent protein.

The vitamin K-dependent protein may be FVII. In one embodiment the FVII is human FVII. In a further embodiment, the FVII is a fusion protein. In a further preferred embodiment, the FVII is an albumin fusion protein. A FVII albumin fusion protein is described, e.g., in WO 2007/090584.

The vitamin K-dependent protein may be Factor IX. In one embodiment, the Factor IX is human Factor IX. In a further embodiment, the Factor IX is a fusion protein. Factor IX may be an albumin fusion protein.

The vitamin K-dependent protein may be Factor X. In one embodiment, the Factor X is human Factor IX. In a further embodiment, the Factor X is a fusion protein. Factor X may be an albumin fusion protein.

The vitamin K-dependent protein may also be any one of FII, Protein C, Protein S, Protein Z, osteocalcin, the calcification inhibiting matrix Gla protein (MGP) and the cell growth regulating growth arrest specific protein 6 (Gas6). In one embodiment, the vitamin K-dependent protein is human protein. In a further embodiment, the vitamin K-dependent protein is a fusion protein. The vitamin K-dependent protein may be an albumin fusion protein.

In one embodiment, the cell culture is a batch culture. The culture is inoculated with an appropriate number of host cells and basal medium. In a batch culture, the cells grow in the basal medium throughout cultivation.

In another embodiment, the cell culture is a fed-batch culture. The culture is inoculated with an appropriate number of host cells and basal medium. Feed medium is added during cultivation in order to replenish nutrients and/or supplements. In one embodiment, the feed is added continuously. In another embodiment, the feed is added periodically. The addition of the feed may start at day 0, day 1 or any later time point from the time point of inoculating the culture. Further, multiple different feeds comprising different nutrients or supplements may be added independently of each other to the cell culture. In one embodiment, the nutrient or supplement status of the culture is monitored throughout cultivation and the feed is added depending on the requirements of the culture.

In another embodiment, the cell culture is a perfusion culture. The culture is inoculated with an appropriate number of host cells and basal medium. Perfusion medium is added during cultivation in order to replenish nutrients and/or in order to compensate for medium removed by harvesting. In one embodiment, the perfusion medium is added continuously. The perfusion medium may be added at a rate of 0.5 to 2 culture volumes per day. In another embodiment, the perfusion medium is added semi-continuously.

In one embodiment, the host cells expressing the vitamin K-dependent protein are cultured for a time period of at least 5 days, preferably for a time period of at least 7 days, most preferably for a time period of at least 9 days.

In one embodiment, L-glutathione is provided at a concentration of 0.5-13 mmol/L, preferably 2-10 mmol/L, more preferably 3.75-7.5 mmol/L in the cell culture. In one embodiment, alpha-ketoglutaric acid is provided at a concentration of 5-50 mmol/L, preferably 10-40 mmol/L, more preferably 15-30 mmol/L in the cell culture. In one embodiment, succinic acid is provided at a concentration of 2-50 mmol/L, preferably 5-30 mmol/L, more preferably 7.5-15 mmol/L in the cell culture. In one embodiment, oxaloacetic acid is provided at a concentration of 5-50 mmol/L, preferably 10-40 mmol/L, more preferably 15-30 mmol/L in the cell culture. In one embodiment, malic acid is provided at a concentration of 5-50 mmol/L, preferably 7.5-30 mmol/L, more preferably 10-20 mmol/L in the cell culture. In one embodiment, fumaric acid is provided at a concentration of 2-50 mmol/L, preferably 5-30 mmol/L, more preferably 7.5-15 mmol/L in the cell culture. In one embodiment, citric acid is provided at a concentration of 0.5-20 mmol/L, preferably 1-15 mmol/L, more preferably 1.5-3.75 mmol/L in the cell culture.

In one embodiment, L-glutathione is provided at a concentration of at least 0.5 mmol/L, preferably at least 2 mmol/L, more preferably at least 3.75 mmol/L in the cell culture. In one embodiment, alpha-ketoglutaric acid is provided at a concentration of at least 5 mmol/L, preferably at least 10 mmol/L, more preferably at least 15 mmol/L in the cell culture. In one embodiment, succinic acid is provided at a concentration of at least 2 mmol/L, preferably at least 5 mmol/L, more preferably at least 7.5 mmol/L in the cell culture. In one embodiment, oxaloacetic acid is provided at a concentration of at least 5 mmol/L, preferably at least 10 mmol/L, more preferably at least 15 mmol/L in the cell culture. In one embodiment, malic acid is provided at a concentration of at least 5 mmol/L, preferably at least 7.5 mmol/L, more preferably at least 10 mmol/L in the cell culture. In one embodiment, fumaric acid is provided at a concentration of at least 2 mmol/L, preferably at least 5 mmol/L, more preferably at least 7.5 mmol/L in the cell culture. In one embodiment, citric acid is provided at a concentration of at least 0.5 mmol/L, preferably at least 1 mmol/L, more preferably at least 1.5 mmol/L in the cell culture.

In a preferred embodiment, alpha-ketoglutaric acid is provided in the cell culture. In the cell culture, one or more of the group consisting of L-glutathione, alpha-ketoglutaric acid, succinic acid, oxaloacetic acid, malic acid, fumaric acid and citric acid may be provided at the indicated concentrations and may be combined with each other. In one embodiment, the cell culture medium comprises a combination of any two or more of L-glutathione, alpha-ketoglutaric acid, succinic acid, oxaloacetic acid, malic acid, fumaric acid and citric acid. In a further embodiment, alpha-ketoglutaric acid is combined with one or more of L-glutathione, succinic acid, oxaloacetic acid, malic acid, fumaric acid and citric acid.

The basal medium may be any standard commercially available cell culture basal medium comprising at least the minimal amounts of nutrients required for cell growth. In one embodiment, the basal medium is serum-free. In a preferred embodiment, the basal medium is chemically defined. In another preferred embodiment, the basal medium is free of proteins from animal or human origin. In a further preferred embodiment, the basal medium is protein-free.

In one embodiment, L-glutathione is provided at a concentration of 0.5-13 mmol/L, preferably 2-10 mmol/L, more preferably 3.75-7.5 mmol/L in the basal medium. In one embodiment, alpha-ketoglutaric acid is provided at a concentration of 5-50 mmol/L, preferably 10-40 mmol/L, more preferably 15-30 mmol/L in the basal medium. In one embodiment, succinic acid is provided at a concentration of 2-50 mmol/L, preferably 5-30 mmol/L, more preferably 7.5-15 mmol/L in the basal medium. In one embodiment, oxaloacetic acid is provided at a concentration of 5-50 mmol/L, preferably 10-40 mmol/L, more preferably 15-30 mmol/L in the basal medium. In one embodiment, malic acid is provided at a concentration of 5-50 mmol/L, preferably 7.5-30 mmol/L, more preferably 10-20 mmol/L in the basal medium. In one embodiment, fumaric acid is provided at a concentration of 2-50 mmol/L, preferably 5-30 mmol/L, more preferably 7.5-15 mmol/L in the basal medium. In one embodiment, citric acid is provided at a concentration of 0.5-20 mmol/L, preferably 1-15 mmol/L, more preferably 1.5-3.75 mmol/L in the basal medium.

In the basal medium, one or more of the group consisting of L-glutathione, alpha-ketoglutaric acid, succinic acid, oxaloacetic acid, malic acid, fumaric acid and citric acid may be provided at the indicated concentrations and may be combined with each other.

The feed medium may be any standard commercially available feed medium comprising nutrients and supplements that are consumed during cell cultivation in high concentrations. In one embodiment, the feed medium is serum-free. In a preferred embodiment, the feed medium is chemically defined. In another preferred embodiment, the feed medium is free of proteins from animal or human origin. In a further preferred embodiment, the feed medium is protein-free.

In one embodiment, the cell culture enhancing reagent is provided in the basal medium and a feed medium is added to the cell culture, wherein the feed medium comprises nutrients that are consumed during cell culture.

The feed medium may comprise one or more of L-glutathione, alpha-ketoglutaric acid, succinic acid, oxaloacetic acid, malic acid, fumaric acid and citric acid. In one embodiment, the feed medium is added to the cell culture in an amount sufficient to maintain the concentration of the respective cell culture enhancing reagent in the cell culture. In one embodiment, L-glutathione is maintained above a concentration of 0.5 mmol/L, preferably above a concentration of 2 mmol/L, more preferably above a concentration of 3.75 mmol/L in the cell culture. In a further embodiment, the concentration of L-glutathione is maintained at a concentration between 0.5-13 mmol/L, preferably between 2-10 mmol/L, more preferably between 3.75-7.5 mmol/L in the cell culture. In one embodiment, alpha-ketoglutaric acid is maintained above a concentration of 5 mmol/L, preferably above a concentration of 10 mmol/L, more preferably above a concentration of 15 mmol/L in the cell culture. In a further embodiment, the concentration of alpha-ketoglutaric acid is maintained at a concentration between 5-50 mmol/L, preferably between 10-40 mmol/L, more preferably between 15-30 mmol/L in the cell culture. In one embodiment, succinic acid is maintained above a concentration of 2 mmol/L, preferably above a concentration of 5 mmol/L, more preferably above a concentration of 7.5 mmol/L in the cell culture. In a further embodiment, the concentration of succinic acid is maintained at a concentration between 2-50 mmol/L, preferably between 5-30 mmol/L, more preferably between 7.5-15 mmol/L in the cell culture. In one embodiment, oxaloacetic acid is maintained above a concentration of 5 mmol/L, preferably above a concentration of 10 mmol/L, more preferably above a concentration of 15 mmol/L in the cell culture. In a further embodiment, the concentration of oxaloacetic acid is maintained at a concentration between 5-50 mmol/L, preferably between 10-40 mmol/L, more preferably between 15-30 mmol/L in the cell culture. In one embodiment, malic acid is maintained above a concentration of 5 mmol/L, preferably above a concentration of 7.5 mmol/L, more preferably above a concentration of 10 mmol/L in the cell culture. In a further embodiment, the concentration of malic acid is maintained at a concentration between 5-50 mmol/L, preferably between 7.5-30 mmol/L, more preferably between 10-20 mmol/L in the cell culture. In one embodiment, fumaric acid is maintained above a concentration of 2 mmol/L, preferably above a concentration of 5 mmol/L, more preferably above a concentration of 7.5 mmol/L in the cell culture. In a further embodiment, the concentration of fumaric acid is maintained at a concentration between 2-50 mmol/L, preferably between 5-30 mmol/L, more preferably between 7.5-15 mmol/L in the cell culture. In one embodiment, citric acid is maintained above a concentration of 0.5 mmol/L, preferably above a concentration of 1 mmol/L, more preferably above a concentration of 1.5 mmol/L in the cell culture. In a further embodiment, the concentration of citric acid is maintained at a concentration between 0.5-20 mmol/L, preferably between 1-15 mmol/L, more preferably between 1.5-3.75 mmol/L in the cell culture.

In the feed medium, one or more of the group consisting of L-glutathione, alpha-ketoglutaric acid, succinic acid, oxaloacetic acid, malic acid, fumaric acid and citric acid may be combined with each other.

The perfusion medium may be any standard perfusion medium. The perfusion medium may be identical to the basal medium. In one embodiment, the perfusion medium is serum-free. In a preferred embodiment, the perfusion medium is chemically defined. In another preferred embodiment, the perfusion medium is free of proteins from animal or human origin. In a further preferred embodiment, the perfusion medium is protein-free.

In one embodiment, the perfusion medium comprises one or more of L-glutathione, alpha-ketoglutaric acid, succinic acid, oxaloacetic acid, malic acid, fumaric acid and citric acid. In one embodiment, the perfusion medium is added to the cell culture in an amount sufficient to maintain the concentration of the respective cell culture enhancing reagent in the cell culture. In one embodiment, L-glutathione is maintained above a concentration of 0.5 mmol/L, preferably above a concentration of 2 mmol/L, more preferably above a concentration of 3.75 mmol/L in the cell culture. In a further embodiment, the concentration of L-glutathione is maintained at a concentration between 0.5-13 mmol/L, preferably between 2-10 mmol/L, more preferably between 3.75-7.5 mmol/L in the cell culture. In one embodiment, alpha-ketoglutaric acid is maintained above a concentration of 5 mmol/L, preferably above a concentration of 10 mmol/L, more preferably above a concentration of 15 mmol/L in the cell culture. In a further embodiment, the concentration of alpha-ketoglutaric acid is maintained at a concentration between 5-50 mmol/L, preferably between 10-40 mmol/L, more preferably between 15-30 mmol/L in the cell culture. In one embodiment, succinic acid is maintained above a concentration of 2 mmol/L, preferably above a concentration of 5 mmol/L, more preferably above a concentration of 7.5 mmol/L in the cell culture. In a further embodiment, the concentration of succinic acid is maintained at a concentration between 2-50 mmol/L, preferably between 5-30 mmol/L, more preferably between 7.5-15 mmol/L in the cell culture. In one embodiment, oxaloacetic acid is maintained above a concentration of 5 mmol/L, preferably above a concentration of 10 mmol/L, more preferably above a concentration of 15 mmol/L in the cell culture. In a further embodiment, the concentration of oxaloacetic acid is maintained at a concentration between 5-50 mmol/L, preferably between 10-40 mmol/L, more preferably between 15-30 mmol/L in the cell culture. In one embodiment, malic acid is maintained above a concentration of 5 mmol/L, preferably above a concentration of 7.5 mmol/L, more preferably above a concentration of 10 mmol/L in the cell culture. In a further embodiment, the concentration of malic acid is maintained at a concentration between 5-50 mmol/L, preferably between 7.5-30 mmol/L, more preferably between 10-20 mmol/L in the cell culture. In one embodiment, fumaric acid is maintained above a concentration of 2 mmol/L, preferably above a concentration of 5 mmol/L, more preferably above a concentration of 7.5 mmol/L in the cell culture. In a further embodiment, the concentration of fumaric acid is maintained at a concentration between 2-50 mmol/L, preferably between 5-30 mmol/L, more preferably between 7.5-15 mmol/L in the cell culture. In one embodiment, citric acid is maintained above a concentration of 0.5 mmol/L, preferably above a concentration of 1 mmol/L, more preferably above a concentration of 1.5 mmol/L in the cell culture. In a further embodiment, the concentration of citric acid is maintained at a concentration between 0.5-20 mmol/L, preferably between 1-15 mmol/L, more preferably between 1.5-3.75 mmol/L in the cell culture.

In the perfusion medium, one or more of the group consisting of L-glutathione, alpha-ketoglutaric acid, succinic acid, oxaloacetic acid, malic acid, fumaric acid and citric acid may be combined with each other.

After protein expression, the recombinant vitamin K-dependent protein may be purified from the cell culture. In one embodiment, the vitamin K-dependent protein is secreted into the medium and the vitamin K-dependent protein may be purified from the supernatant. The purification process may therefore involve removal of the host cells and other solids from the cell culture. Such removal can, for example, be achieved by centrifugation or filtration. In one embodiment, the recombinant vitamin K-dependent protein is further purified by chromatography, such as size exclusion chromatography, affinity chromatography, hydrophobic interaction chromatography, ion exchange chromatography and/or multimodal chromatography. The purification process may further involve centrifugation, ethanol precipitation and/or dialysis. In one embodiment, the vitamin K-dependent protein is concentrated after purification. The process may involve further separation and/or isolation steps.

Some methods further comprise measuring chromogenic activity of the vitamin K-dependent protein. In specific embodiments, the recombinant vitamin K-dependent protein has increased chromogenic activity relative to a vitamin K-dependent protein produced under comparable conditions, but where the cell culture medium does not comprises a TCA intermediate and/or L-glutathione.

In one embodiment, the chromogenic activity of FVII prepared according to the method of the invention is increased by 20% in comparison to FVII prepared under comparable conditions, but where the cell culture medium does not comprises a TCA intermediate and/or L-glutathione. In another embodiment, the chromogenic activity of FVII prepared according to the method of the invention is increased by 50% in comparison to FVII prepared under comparable conditions, but where the cell culture medium does not comprises a TCA intermediate and/or L-glutathione. In a further embodiment, the chromogenic activity of FVII prepared according to the method of the invention is increased by 100% in comparison to FVII prepared under comparable conditions, but where the cell culture medium does not comprises a TCA intermediate and/or L-glutathione. In another embodiment, the chromogenic activity of FVII prepared according to the method of the invention is increased by 200% in comparison to FVII prepared under comparable conditions, but where the cell culture medium does not comprises a TCA intermediate and/or L-glutathione.

Some methods further comprise determining the yield of the vitamin K-dependent protein. In specific embodiments, the yield of the recombinant vitamin K-dependent protein is increased relative to a vitamin K-dependent protein produced under comparable conditions, but where the cell culture medium does not comprises a TCA intermediate and/or L-glutathione.

Further provided is the use of L-glutathione, alpha-ketoglutaric acid, succinic acid, oxaloacetic acid, malic acid, fumaric acid and/or citric acid or salts thereof for increasing the yield of a recombinant vitamin K-dependent protein and/or for enhancing the activity of a recombinant vitamin K-dependent protein.

Also provided is the use of a cell culture medium comprising L-glutathione, alpha-ketoglutaric acid, succinic acid, oxaloacetic acid, malic acid, fumaric acid and/or citric acid for increasing the yield of a recombinant vitamin K-dependent protein and/or for enhancing the activity of a recombinant vitamin K-dependent protein.

In one embodiment, the invention relates to a composition of matter comprising host cells comprising an expression system expressing a recombinant vitamin K-dependent protein and a cell culture medium as described herein. Further provided is a bioreactor comprising the composition of matter.

Also provided are pharmaceutical compositions comprising the vitamin K-dependent protein prepared according to the method of the present invention and a pharmaceutically acceptable excipient. Non-limiting examples of pharmaceutically acceptable excipients are pH adjusting agents, buffering agents and tonicity adjusting agents.

A pharmaceutical composition of the invention may be formulated to be compatible with its intended route of administration. Examples of routes of administration include parenteral, e.g., intravenous, intradermal, subcutaneous, oral (e.g., inhalation), transdermal (topical); transmucosal, and rectal administration. Solutions or suspensions used for parenteral, intradermal, or subcutaneous, application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases; such as hydrochloric acid of sodium hydroxide. Further suitable excipients are known from the prior art. The preparation can be enclosed in ampoules, disposable syringes or multiple dose vials made of glass or plastic.

Also provided are medical uses of the vitamin K-dependent protein prepared according to the method of the present invention. In one embodiment, FVII prepared according to the method of the present invention for use in the treatment or prevention of hemophilia A or uncontrollable hemorrhage is provided.

The method provided herein is for increasing the yield of a vitamin K-dependent protein and/or for enhancing the activity of a recombinant vitamin K-dependent protein.

Figure 8A:
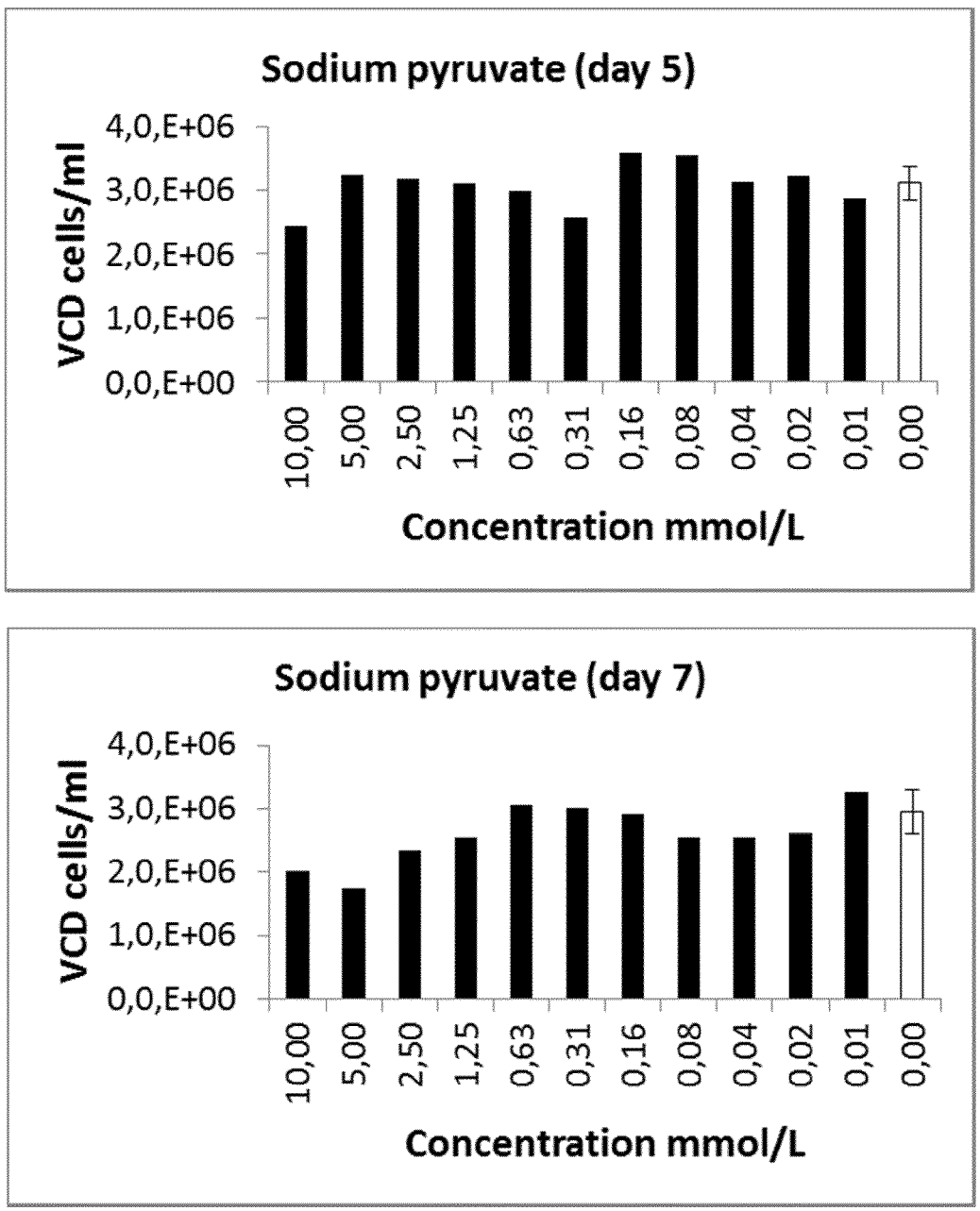
FIG. 8A: Viable cell density of CHO cells expressing FVII that are grown in the presence of different concentrations of sodium pyruvate for 5 or 7 days, respectively (comparative example).
Figure 8B:
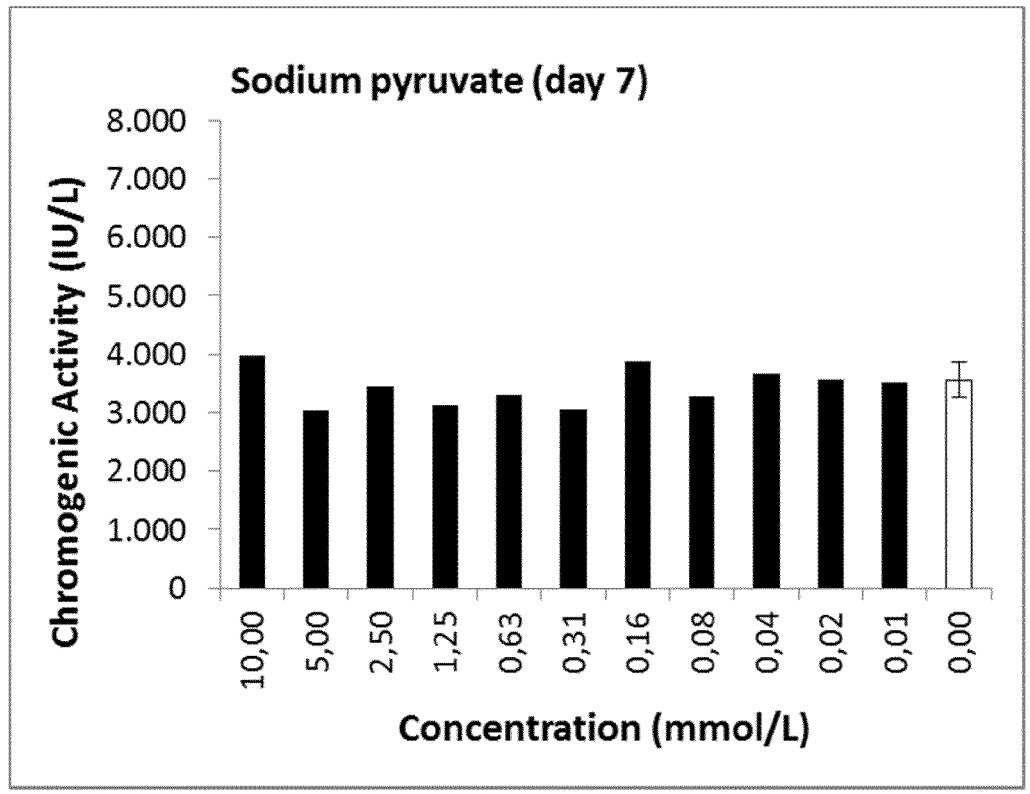
FIGS. 8B+C: Chromogenic activity of FVII obtained from CHO cells expressing FVII that are grown in the presence of different concentrations of sodium pyruvate for 7, 9 or 10 days, respectively (comparative example).
Figure 8B:
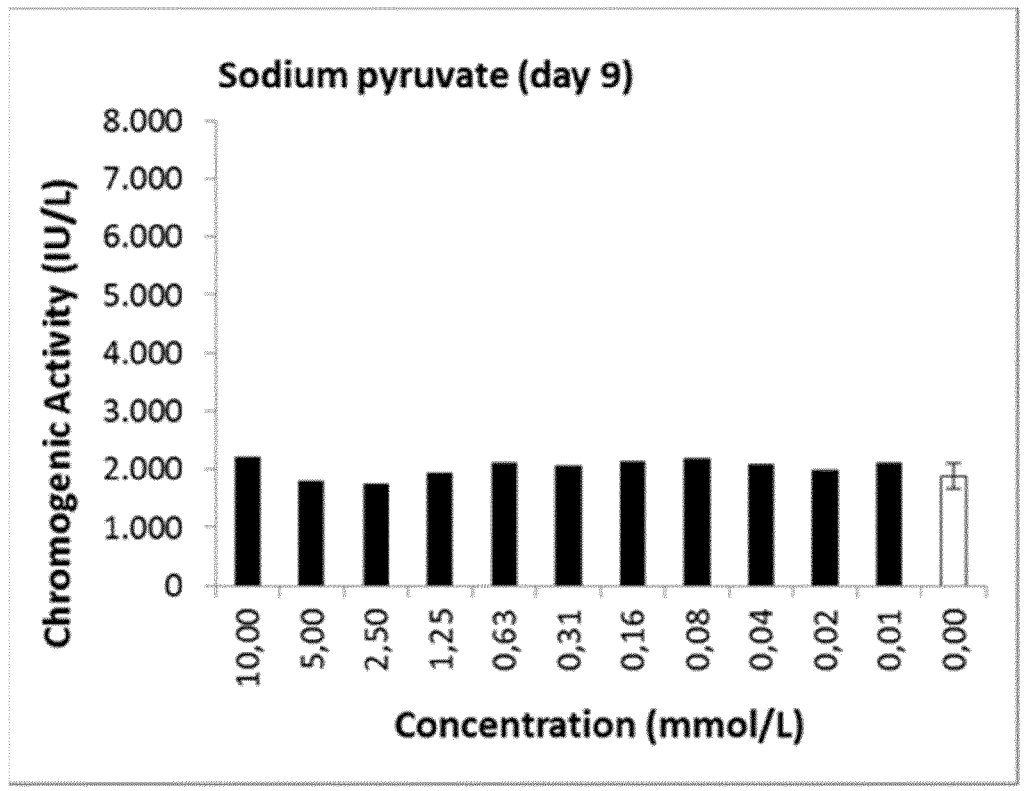
Figure 8C:
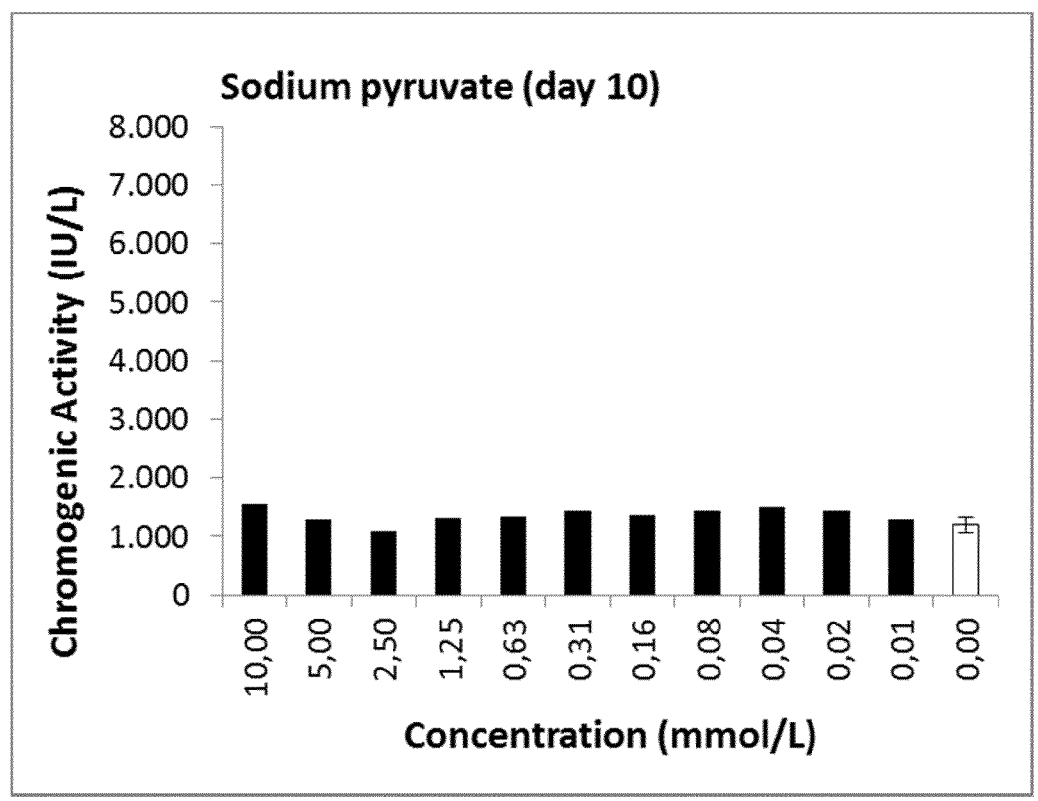

Accordingly, by employing the method of the invention, a vitamin K-dependent protein can be more efficiently prepared than with methods disclosed in the prior art. In particular, the presence of L-glutathione or a TCA intermediate in the cell culture medium during expression of the vitamin K-dependent protein FVII enhances yield and/or activity of FVII (FIGS. 1B, 1C, 2B, 2C, 3B, 3C, 4B, 4C, 5B, 5C, 6B, 6C, 7B and 7C). Sodium pyruvate which was used as a control has no impact on yield and/or activity of FVII (FIGS. 8B and 8C). Generally, the presence of L-glutathione, a TCA intermediate or sodium pyruvate in the cell culture medium has only minor impact on the viable cell density (VCD) (FIGS. 1A, 2A, 3A, 4A, 5A, 6A, 7A and 8A).

Without wanting to be bound by any theory, the following explanation is provided for the achieved effect: For expression of a vitamin K-dependent protein, vitamin K is required for formation of γ-carboxyglutamate (Gla) residues. The γ-carboxylation of glutamic acid is coupled to the vitamin K recycling pathway and dependent on cellular reductive potential. The hypothesis is that the addition of a TCA intermediate to the culture provides an additional source of intermediates feeding into the TCA cycle generating additional NADH (i.e. reductive potential) required to maintain the γ-carboxylation of glutamic acid residues of vitamin K-dependent proteins. Addition of L-glutathione to the culture likewise helps to maintain a favourable redox environment for the γ-carboxylation of glutamic acid.

EXAMPLES

Example 1

Cell Culture

Chinese Hamster Ovary cell line that expresses recombinant human Factor VII fusion protein was created using the GS expression system (Lonza). These cells were maintained in commercially available CD-CHO AGT medium (Invitrogen) supplemented with 50 μg/L reduced menadione sodium bisulfite (rMSB) (Richman), 25 μM methionine sulfoximine (MSX) (Sigma) and 1 mg/L insulin (Novo Nordisk). Cells were grown in shake flasks maintained at 37° C. with 8% $CO_2$ atmosphere and subcultured every 3 days to $3 \times 10^5$ cells/mL.

Cells from the exponential growth phase of the cultures (at the end of regular 3-day passages) were used for the experiments. The cells were centrifuged, appropriate amount of spent media removed and cell pellets were resuspended in remaining spent media to a cell concentration of $3 \times 10^6$ cells/mL. 50 μL of this cell suspension was used to inoculate each well of a polypropylene V-bottom square 96-deepwell plate (Corning) containing 450 μL of a cell culture media based on DMEM/F12 supplemented with different levels of reduced L-glutathione (Sigma). The reduced L-glutathione concentration ranges tested were 0.01-15 mM with a corresponding reduced L-glutathione-free negative control. All cultures contained 213 μg/L rMSB to support appropriate cellular processing of Factor VII. All liquid handling steps were performed using a Tecan Freedom EVO® 200 robotic platform.

Culture plates were sealed with a breathable membrane (Corning) to maintain sterility and cultures were maintained at 37° C. with 8% $CO_2$ atmosphere in a shaker incubator (Kuhner) operating at 350 rpm with an oribital diameter of 25 mm.

Determination of Cell Growth and Viability

The cell density and viability in the culture were determined offline from a sample of culture obtained at day 5 and day 7 (counted from inoculation of the culture) using a MACSQuant® Analyzer 10 flow cytometer (Miltenyi Biotec), utilizing propidium iodide (Miltenyi Biotec) for viability staining. Results are shown in FIG. 1A. The results show that at most concentrations tested, L-glutathione has no effect on the viable cell density.

Quantification of Recombinant Factor VII

Figure 1B:
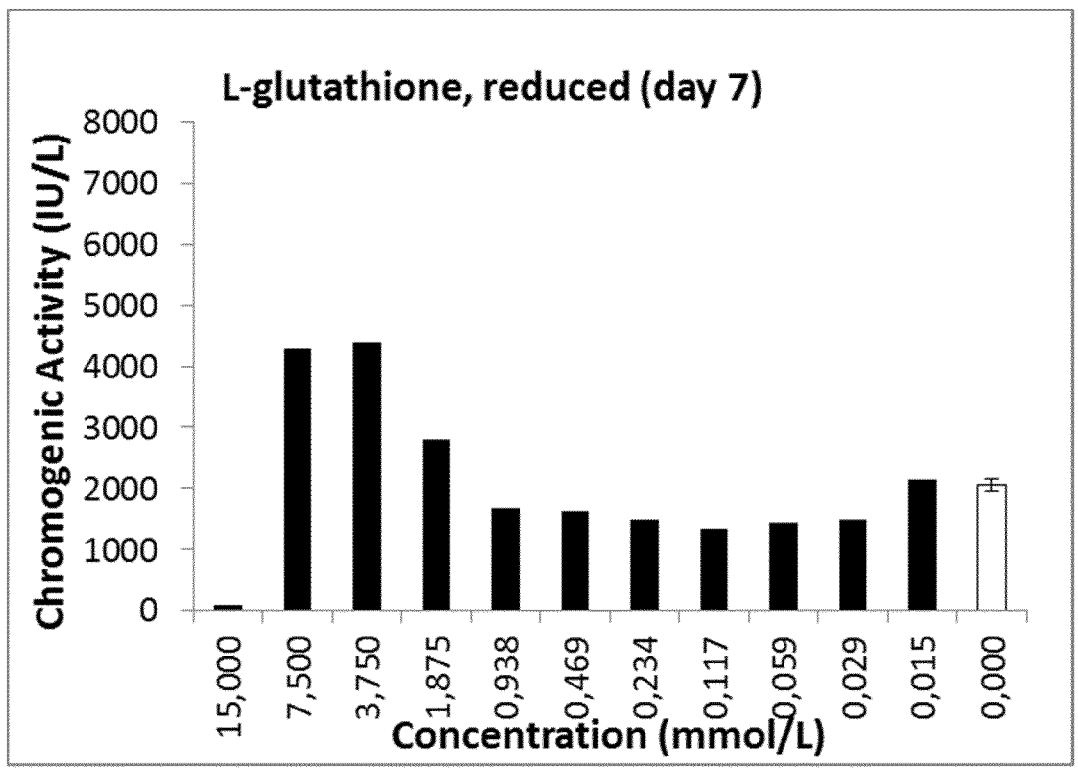
FIGS. 1B+C: Chromogenic activity of FVII obtained from CHO cells expressing FVII that are grown in the presence of different concentrations of reduced L-glutathione for 7, 9 or 10 days, respectively.
Figure 1B:
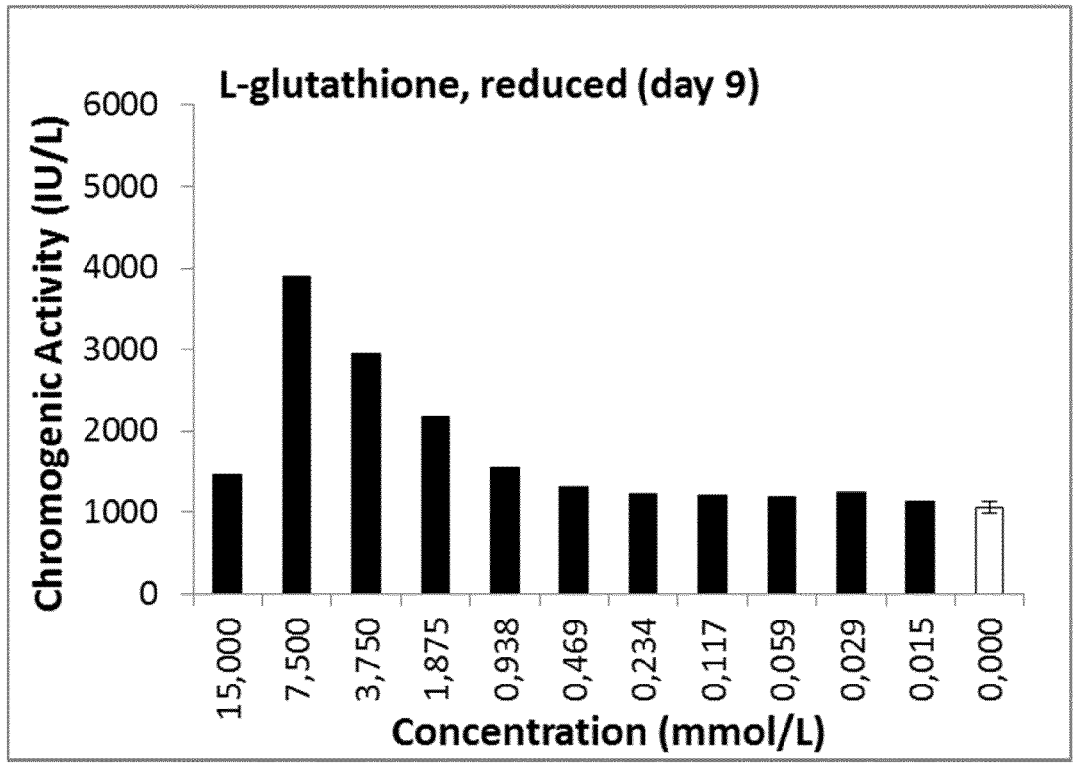
Figure 1C:
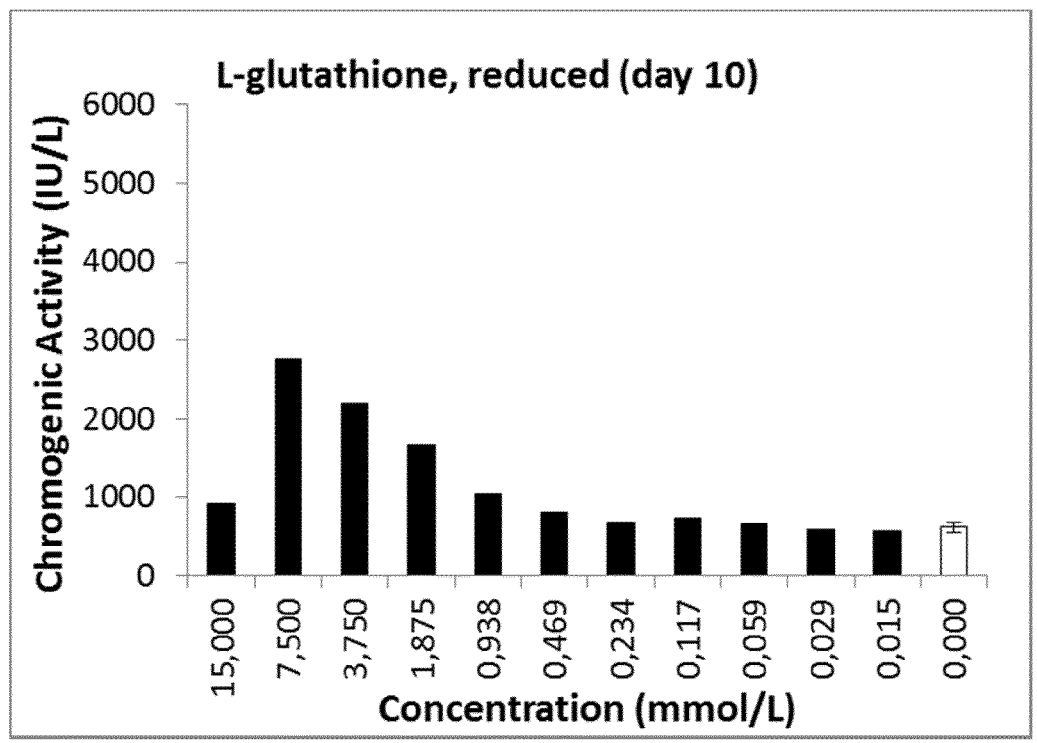
Figure 2A:
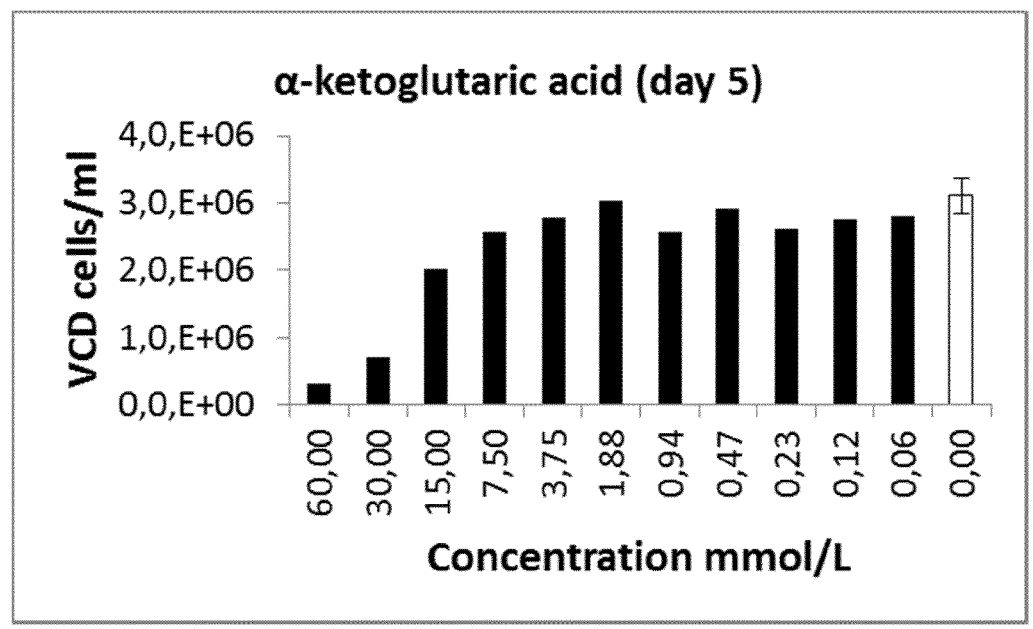
FIG. 2A: Viable cell density of CHO cells expressing FVII that are grown in the presence of different concentrations of alpha-ketoglutaric acid for 5 or 7 days, respectively.
Figure 2A:
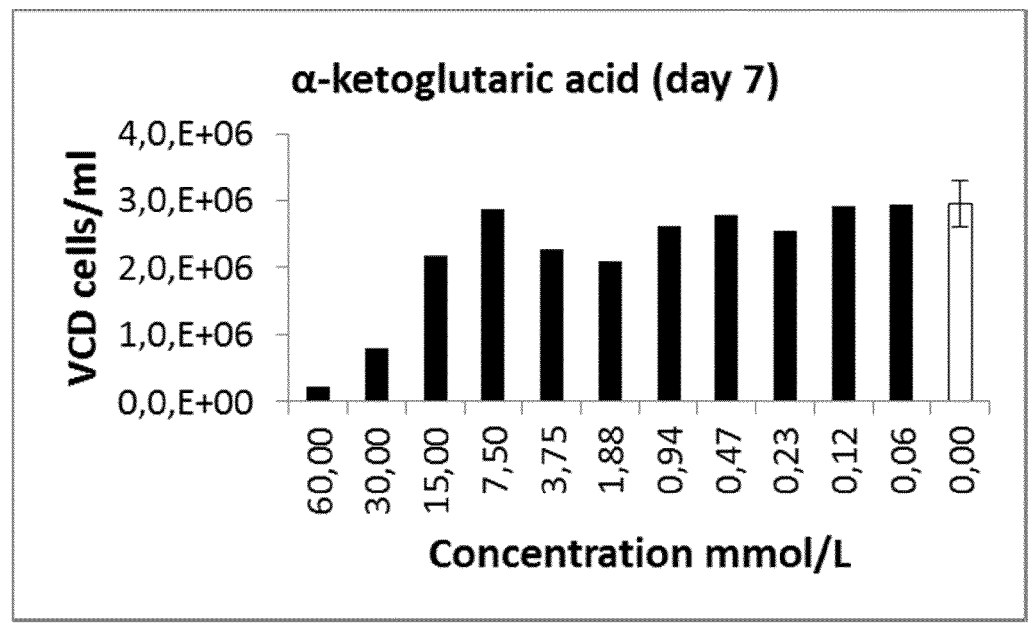
Figure 2B:
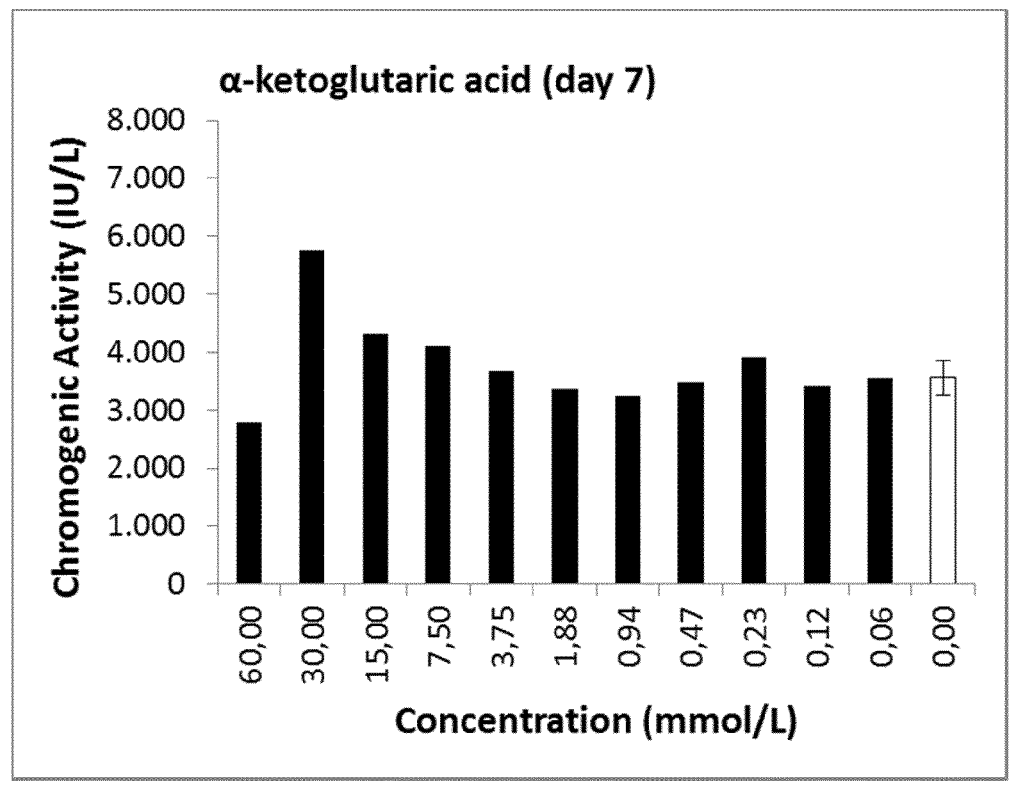
FIGS. 2B+C: Chromogenic activity of FVII obtained from CHO cells expressing FVII that are grown in the presence of different concentrations of alpha-ketoglutaric acid for 7, 9 or 10 days, respectively.
Figure 2B:
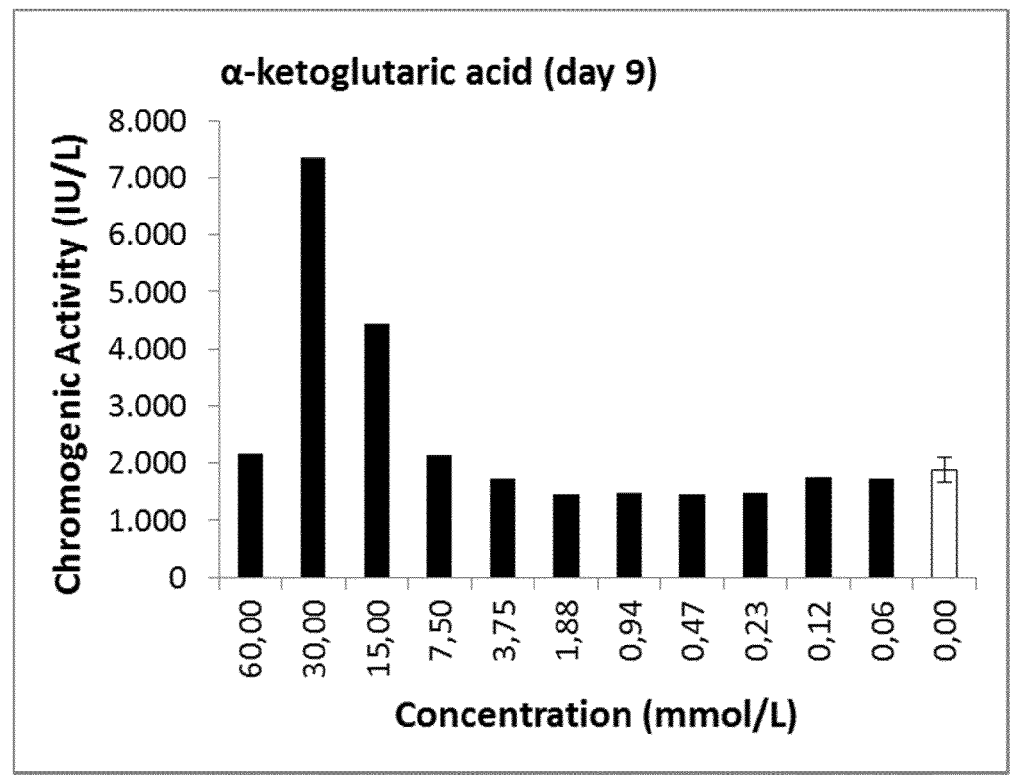
Figure 2C:
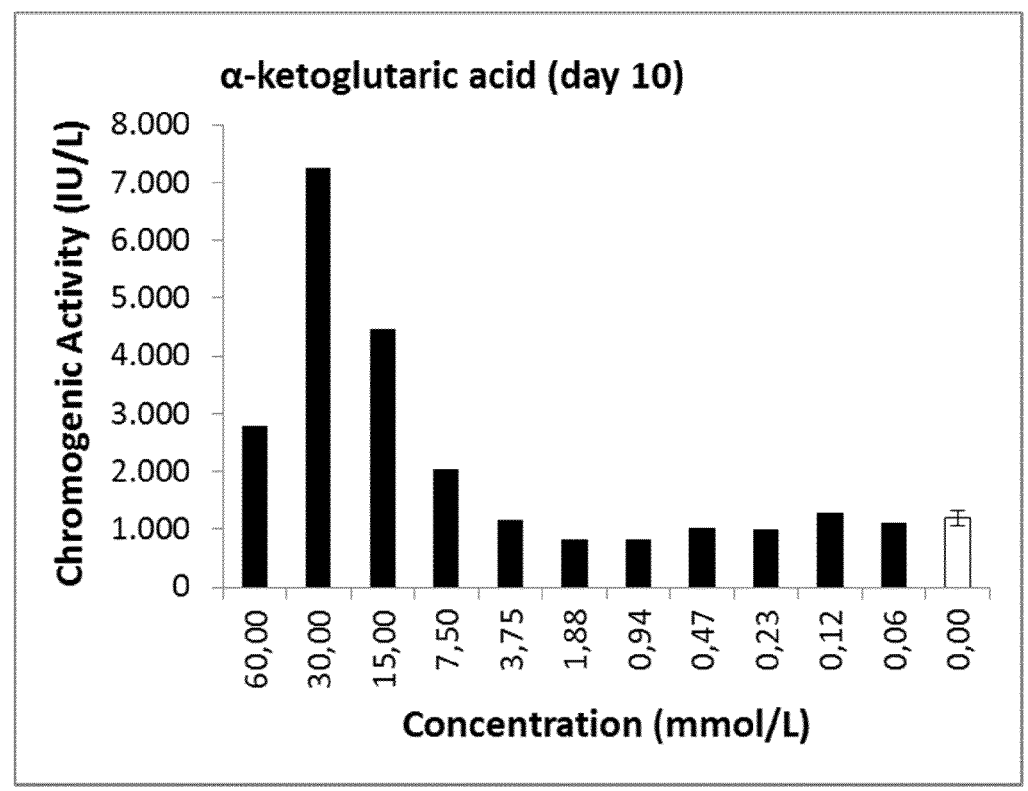
Figure 3A:
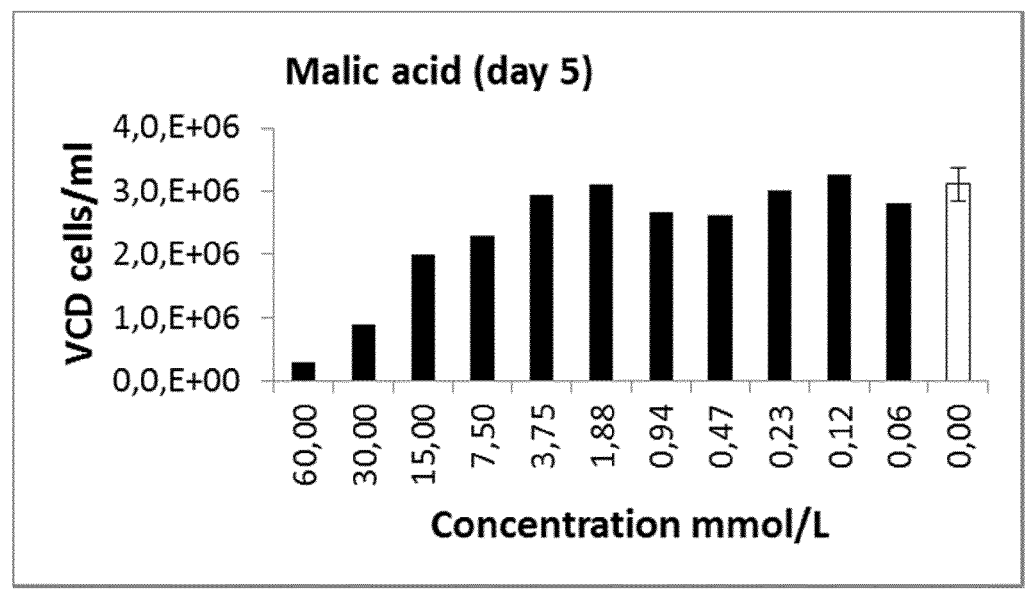
FIG. 3A: Viable cell density of CHO cells expressing FVII that are grown in the presence of different concentrations of malic acid for 5 or 7 days, respectively.
Figure 3A:
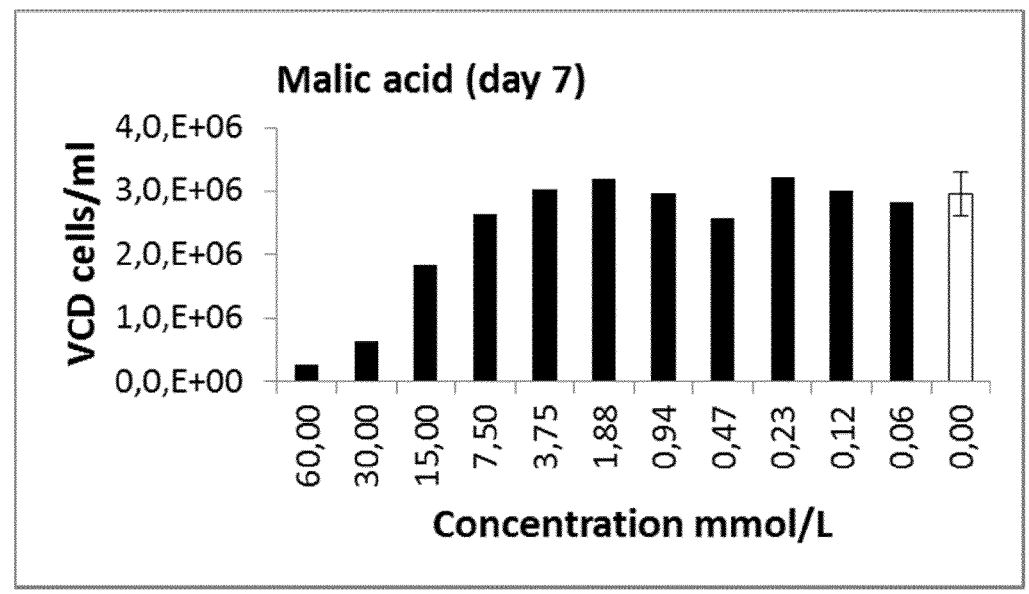
Figure 3B:
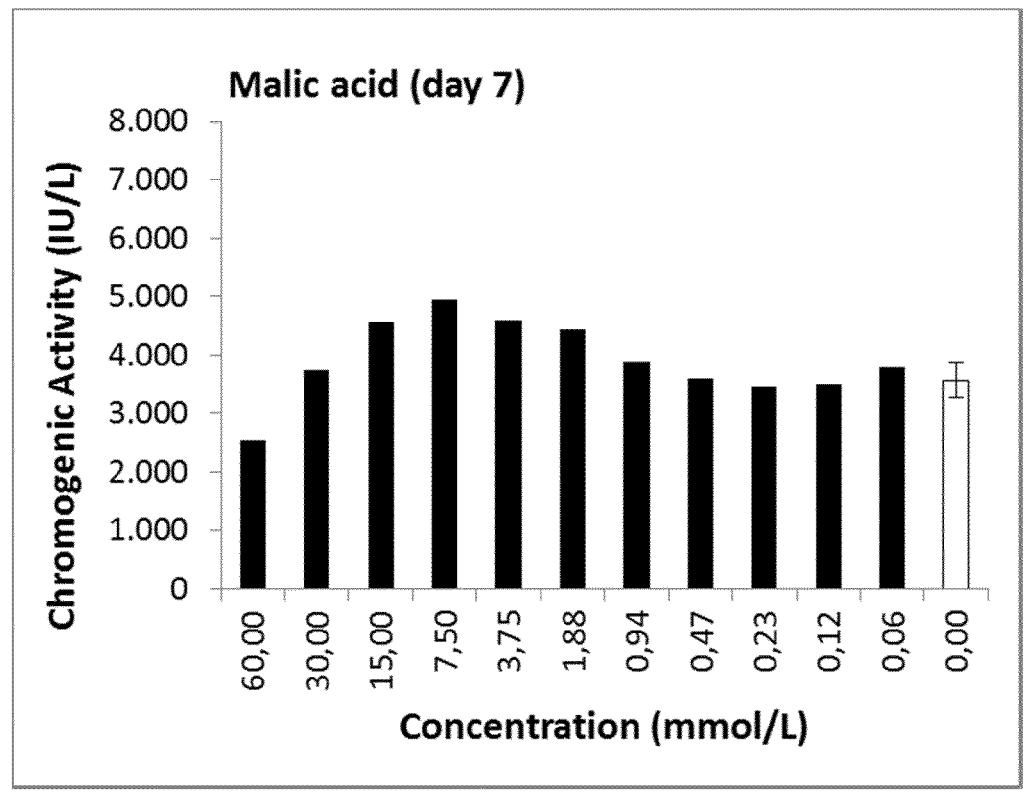
FIGS. 3B+C: Chromogenic activity of FVII obtained from CHO cells expressing FVII that are grown in the presence of different concentrations of malic acid for 7, 9 or 10 days, respectively.
Figure 3B:
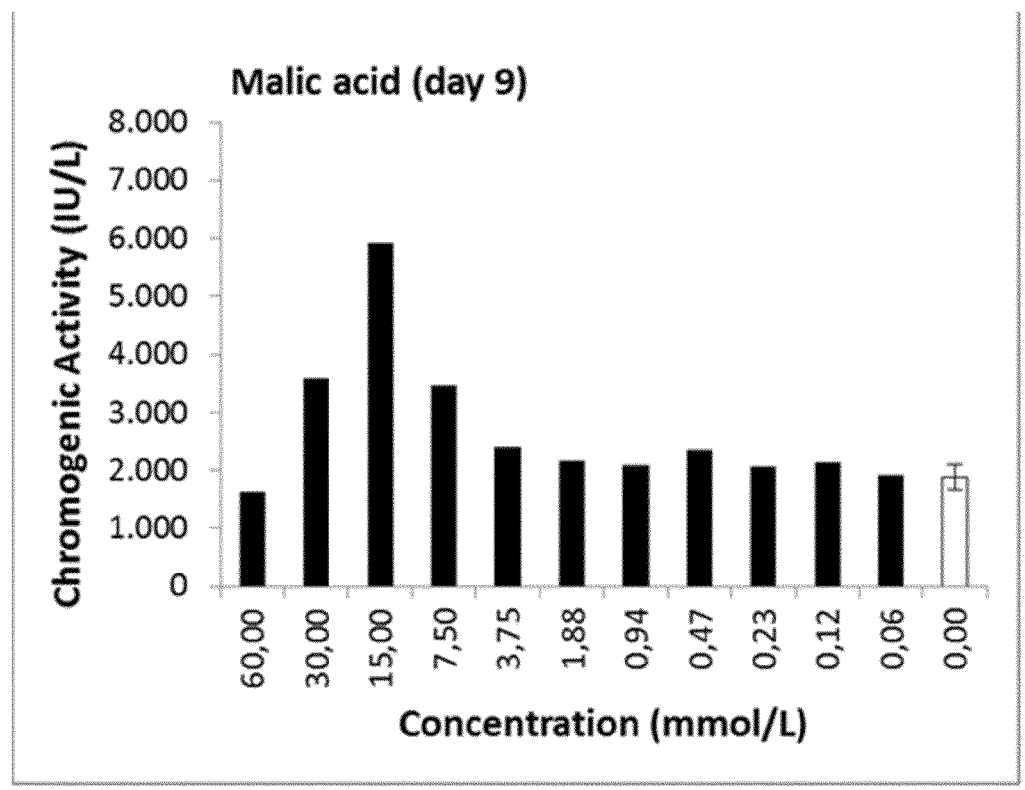
Figure 3C:
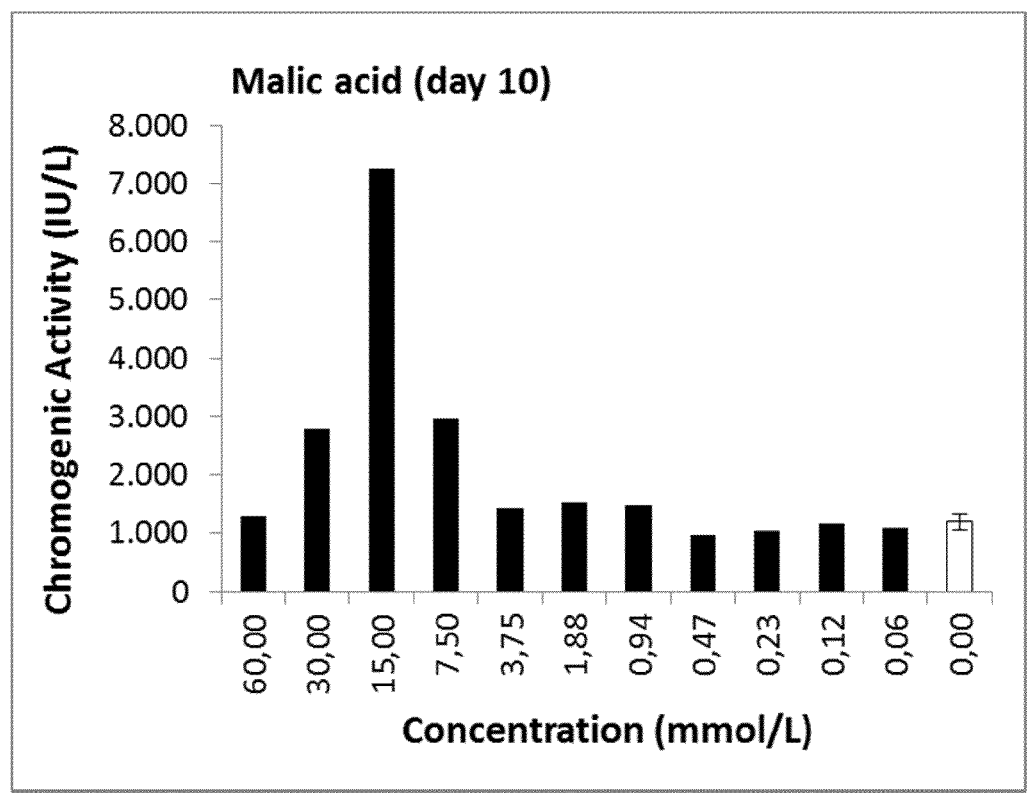
Figure 4A:
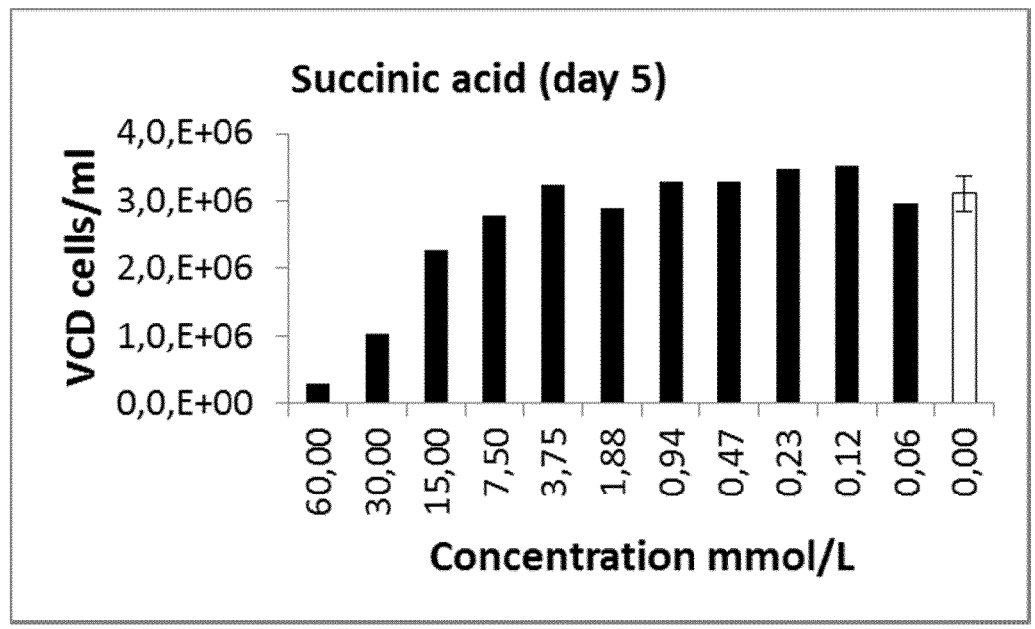
FIG. 4A: Viable cell density of CHO cells expressing FVII that are grown in the presence of different concentrations of succinic acid for 5 or 7 days, respectively.
Figure 4A:
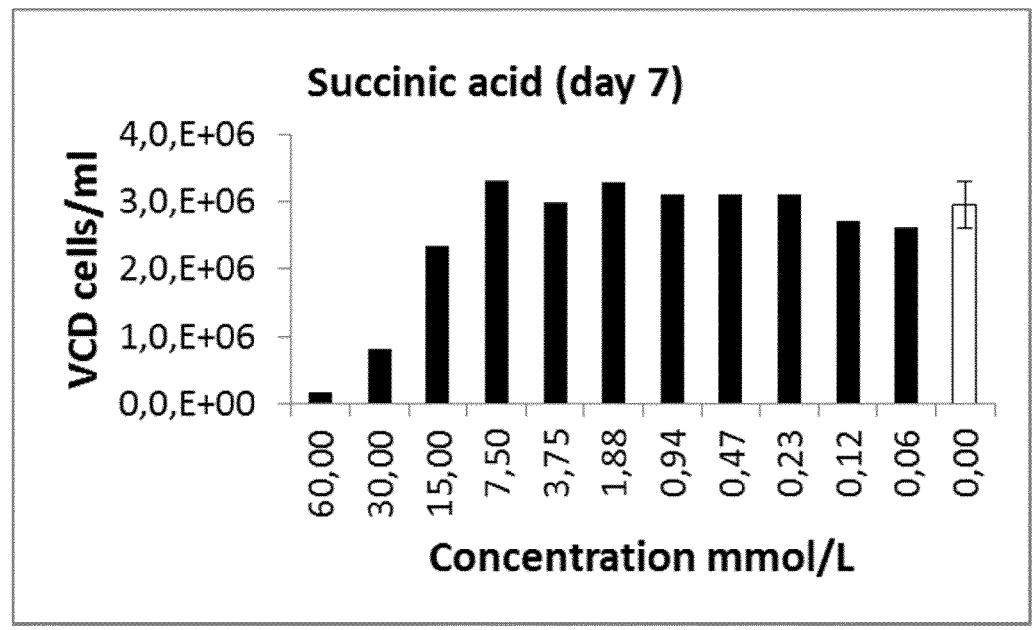
Figure 4B:
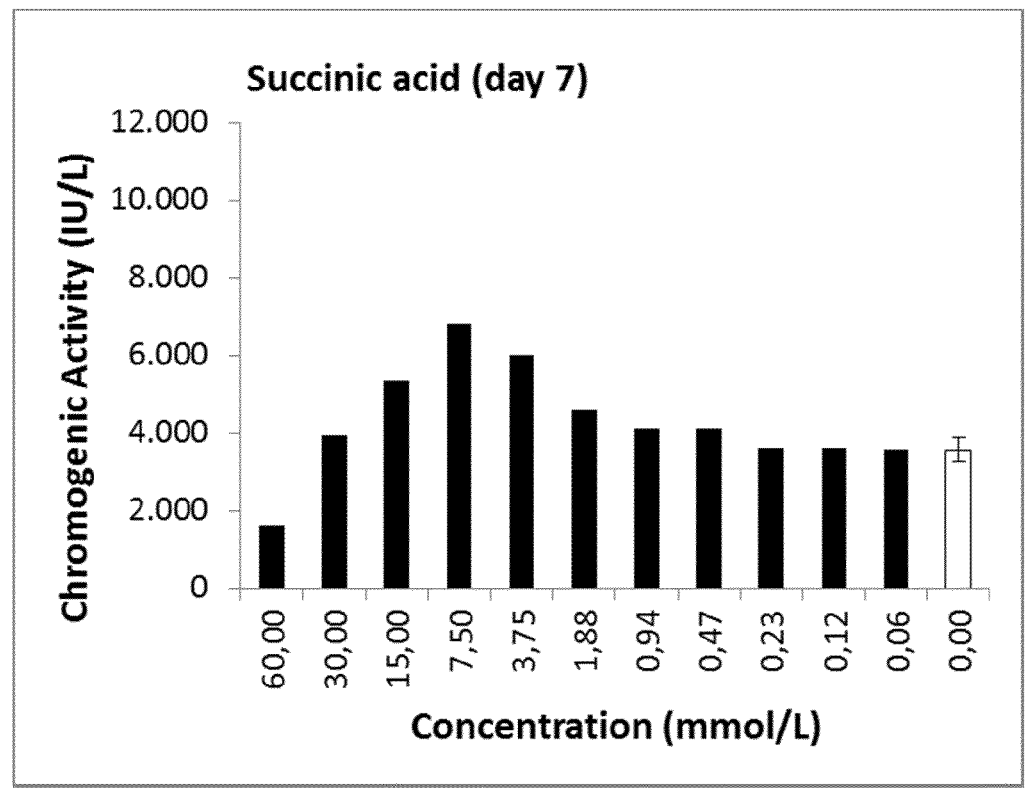
FIGS. 4B+C: Chromogenic activity of FVII obtained from CHO cells expressing FVII that are grown in the presence of different concentrations of succinic acid for 7, 9 or 10 days, respectively.
Figure 4B:
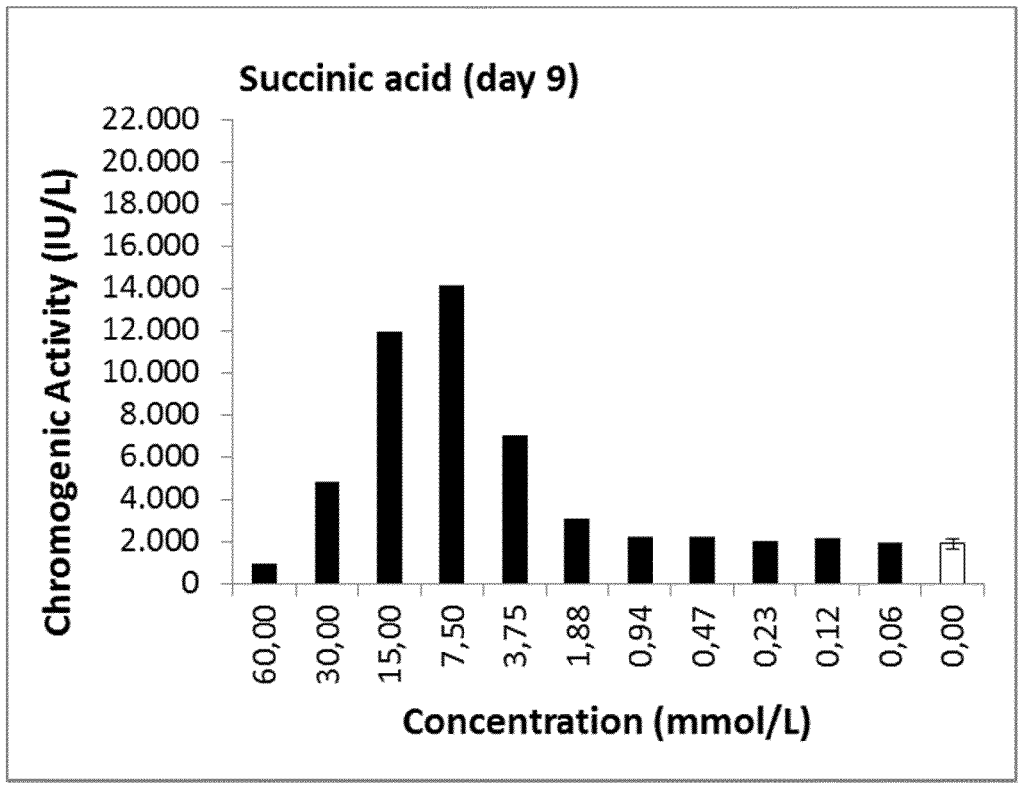
Figure 4C:
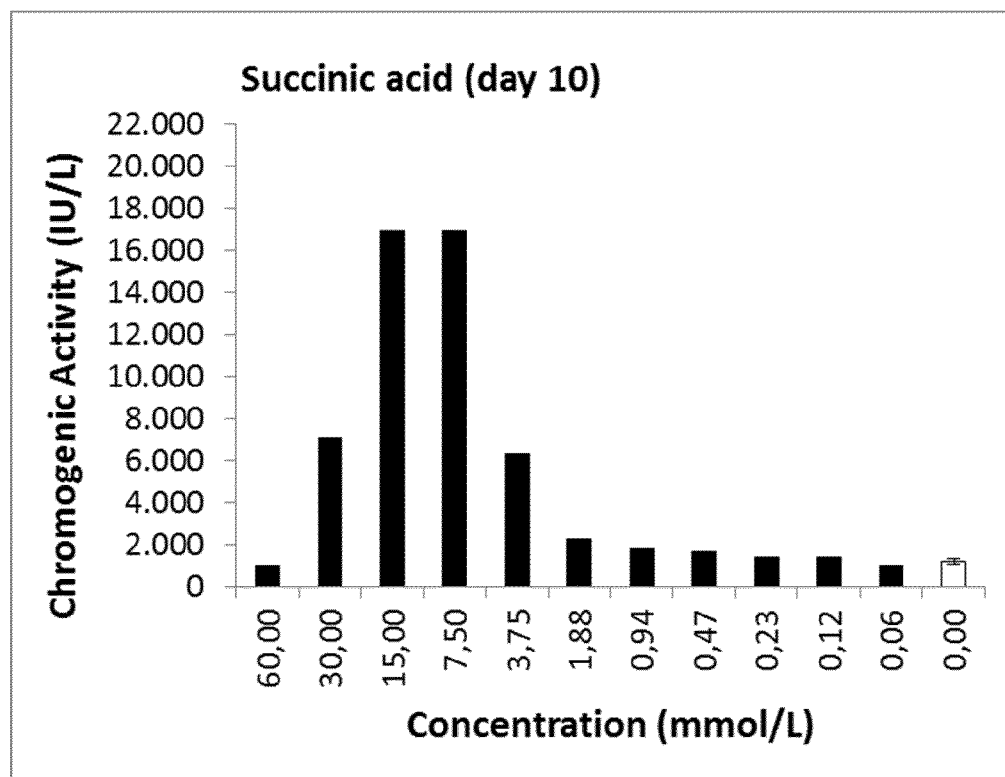
Figure 5A:
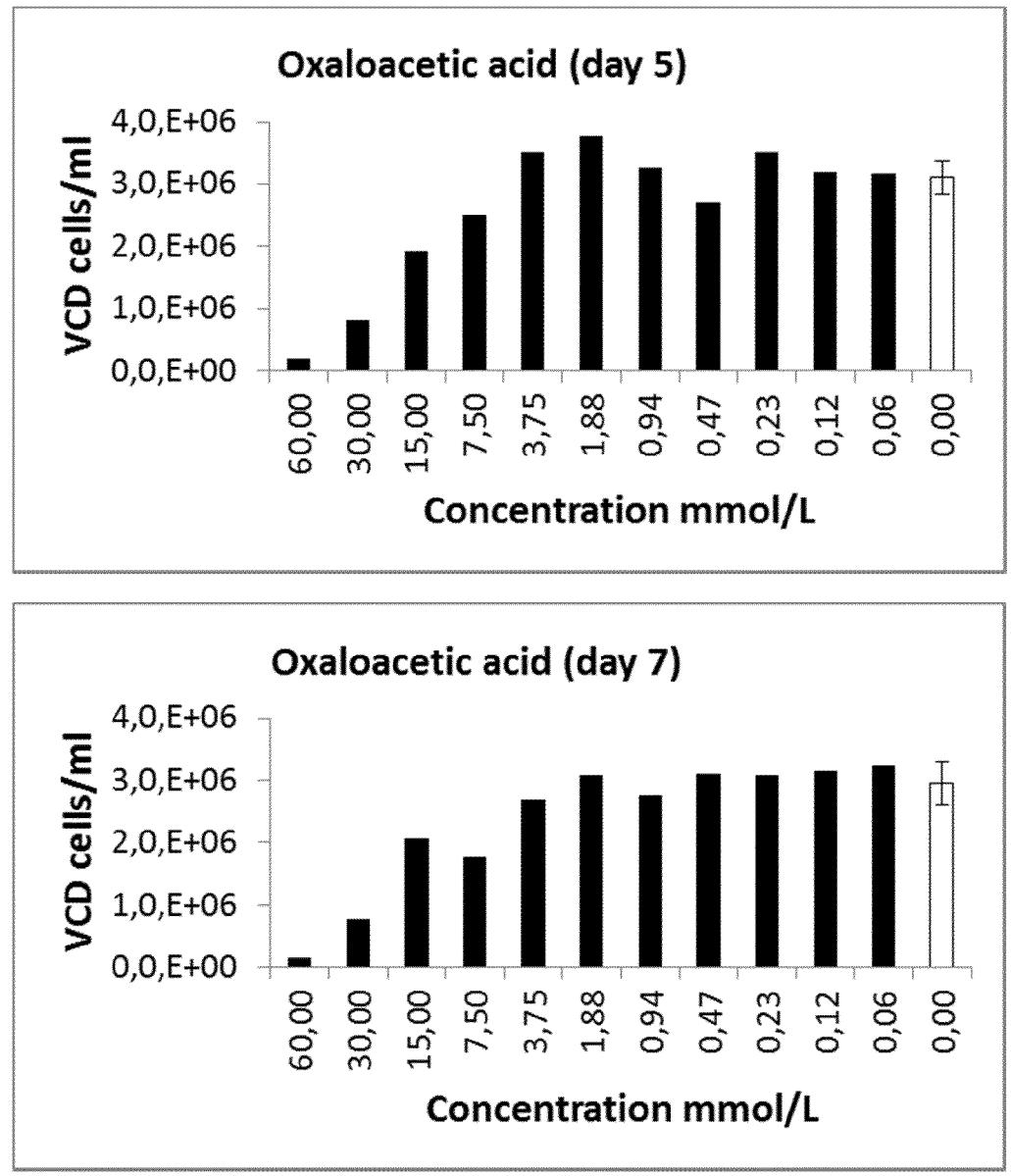
FIG. 5A: Viable cell density of CHO cells expressing FVII that are grown in the presence of different concentrations of oxaloacetic acid for 5 or 7 days, respectively.
Figure 5B:
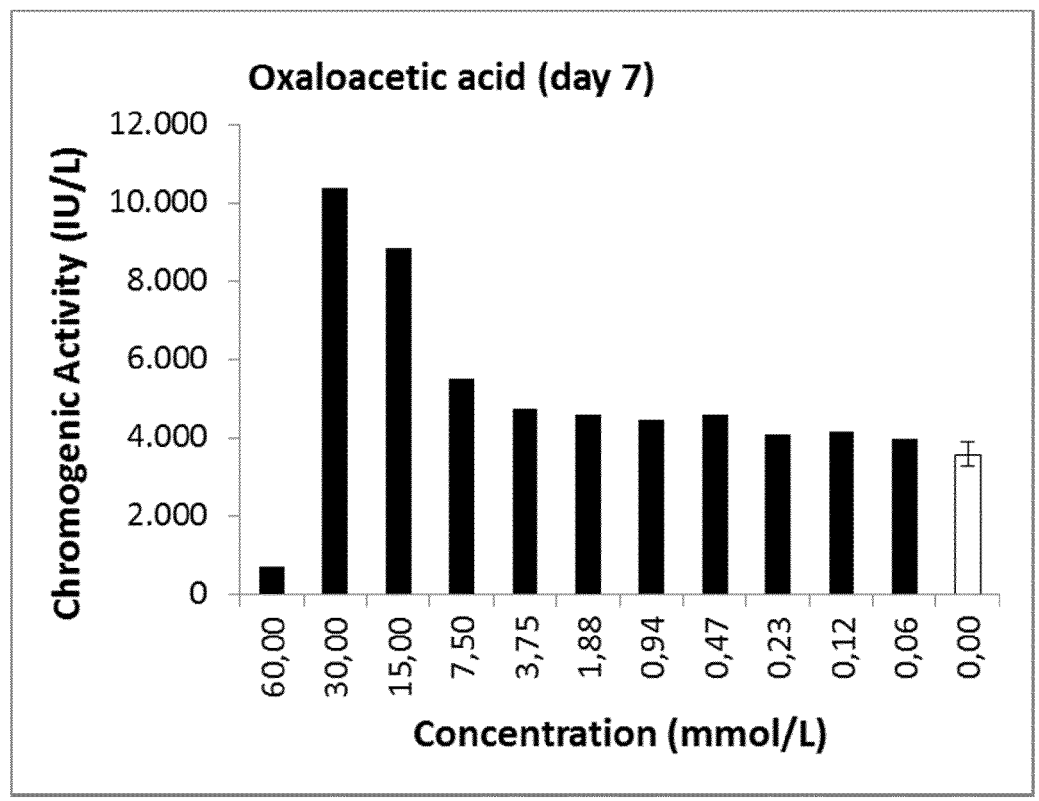
FIGS. 5B+C: Chromogenic activity of FVII obtained from CHO cells expressing FVII that are grown in the presence of different concentrations of oxaloacetic acid for 7, 9 or 10 days, respectively.
Figure 5B:
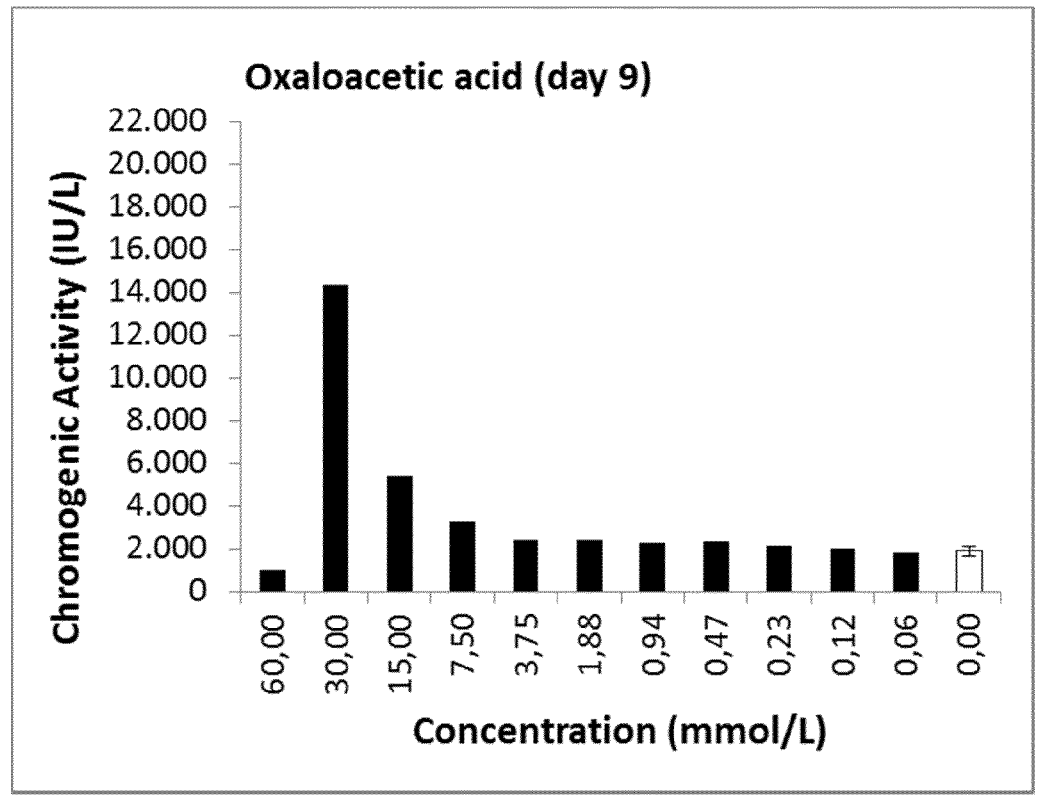
Figure 5C:
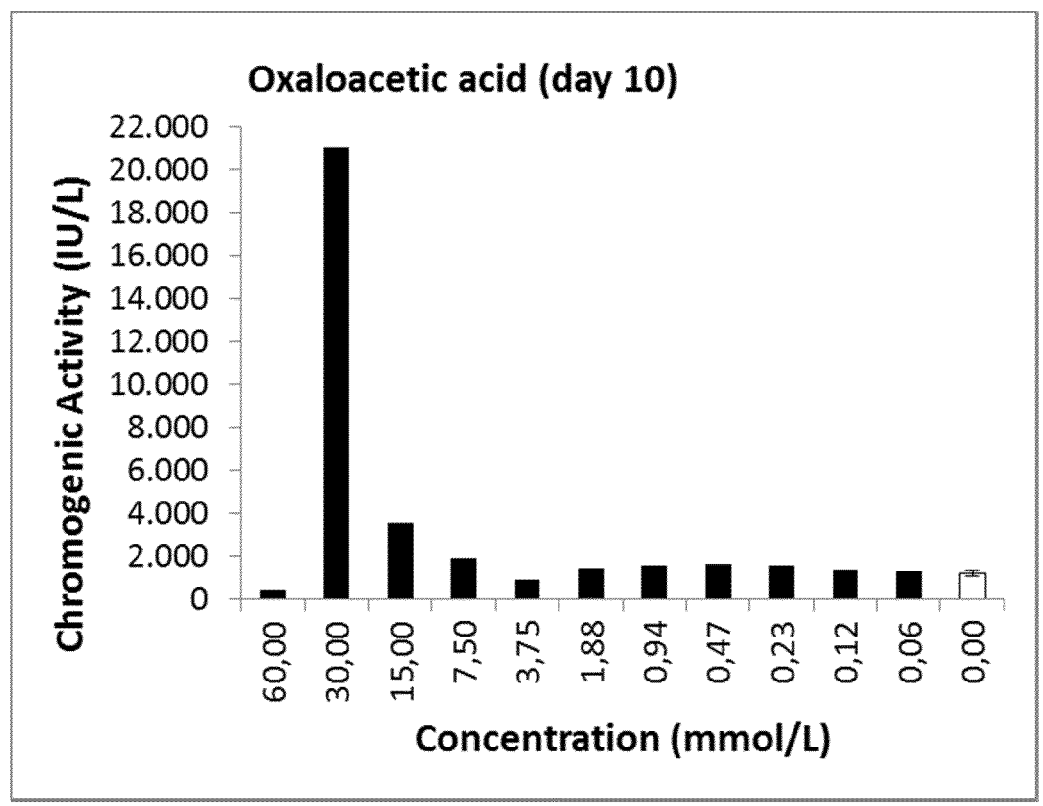
Figure 6A:
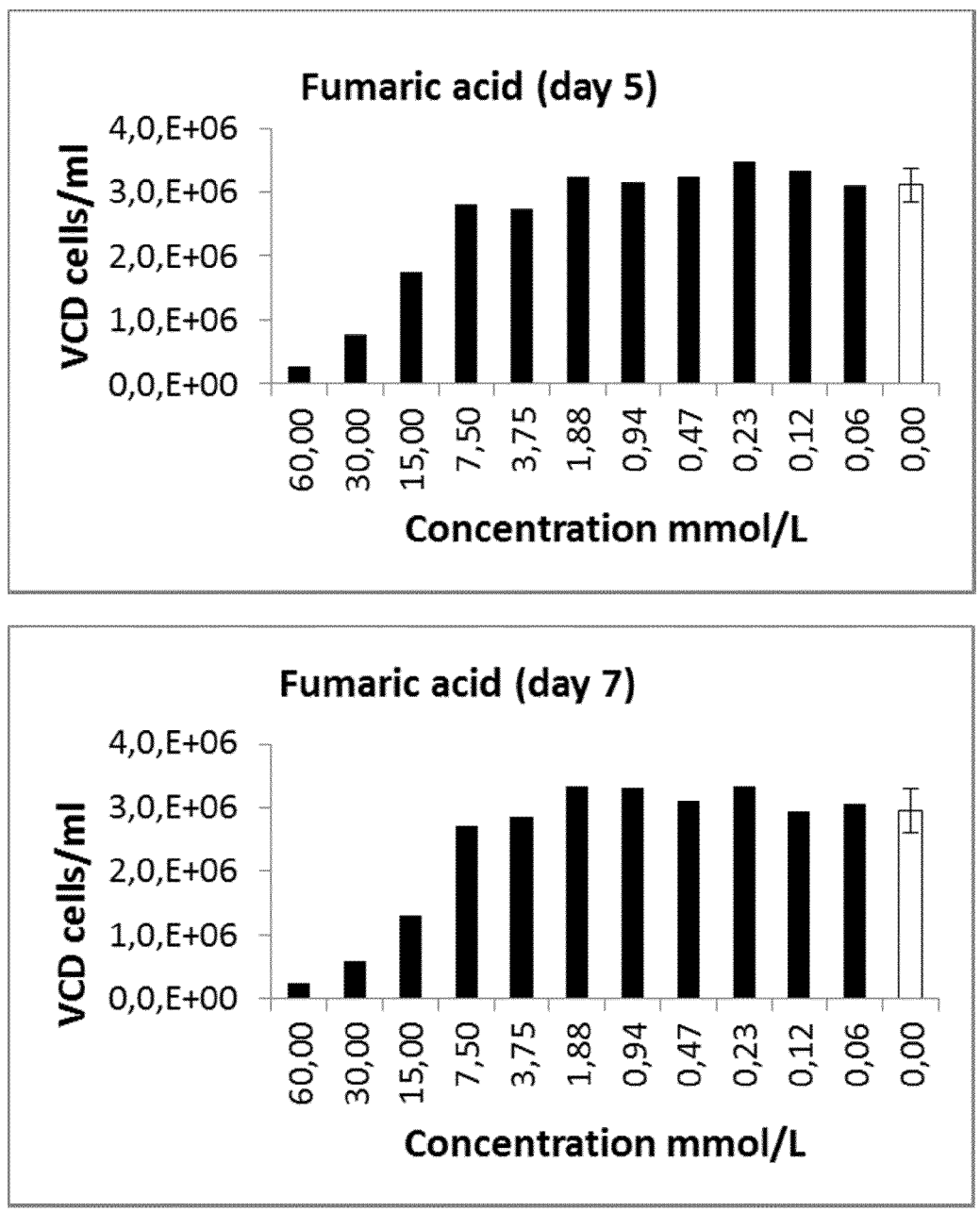
FIG. 6A: Viable cell density of CHO cells expressing FVII that are grown in the presence of different concentrations of fumaric acid for 5 or 7 days, respectively.
Figure 6B:
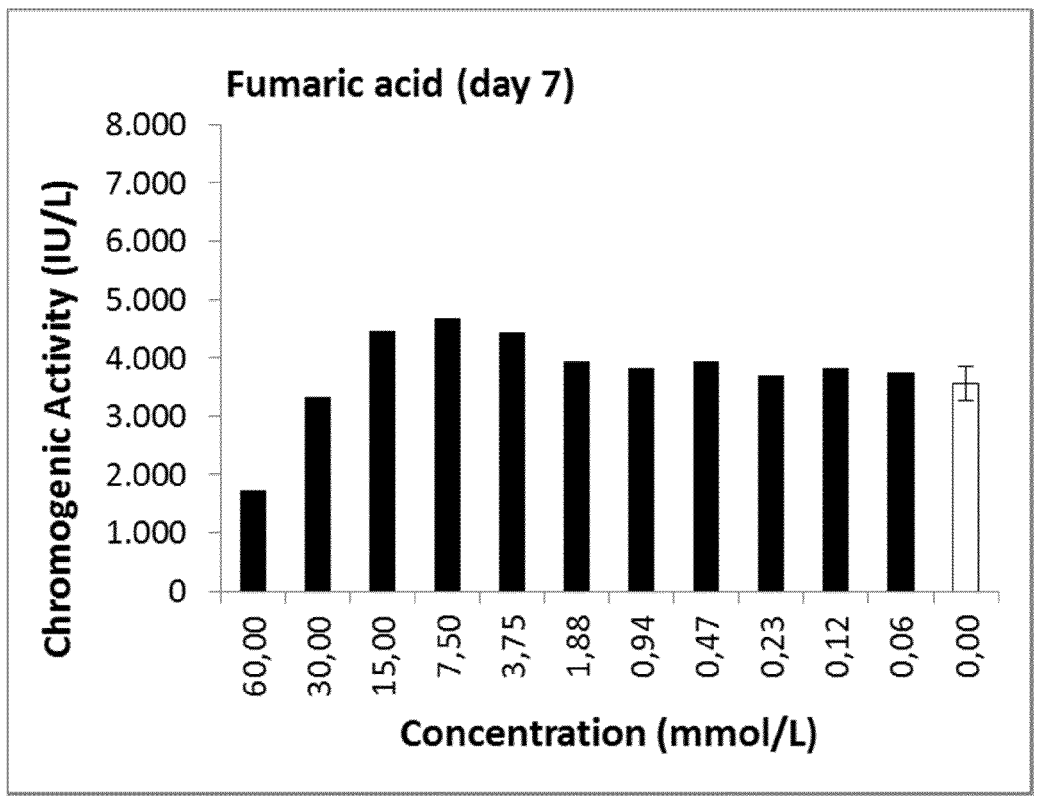
FIGS. 6B+C: Chromogenic activity of FVII obtained from CHO cells expressing FVII that are grown in the presence of different concentrations of fumaric acid for 7, 9 or 10 days, respectively.
Figure 6B:
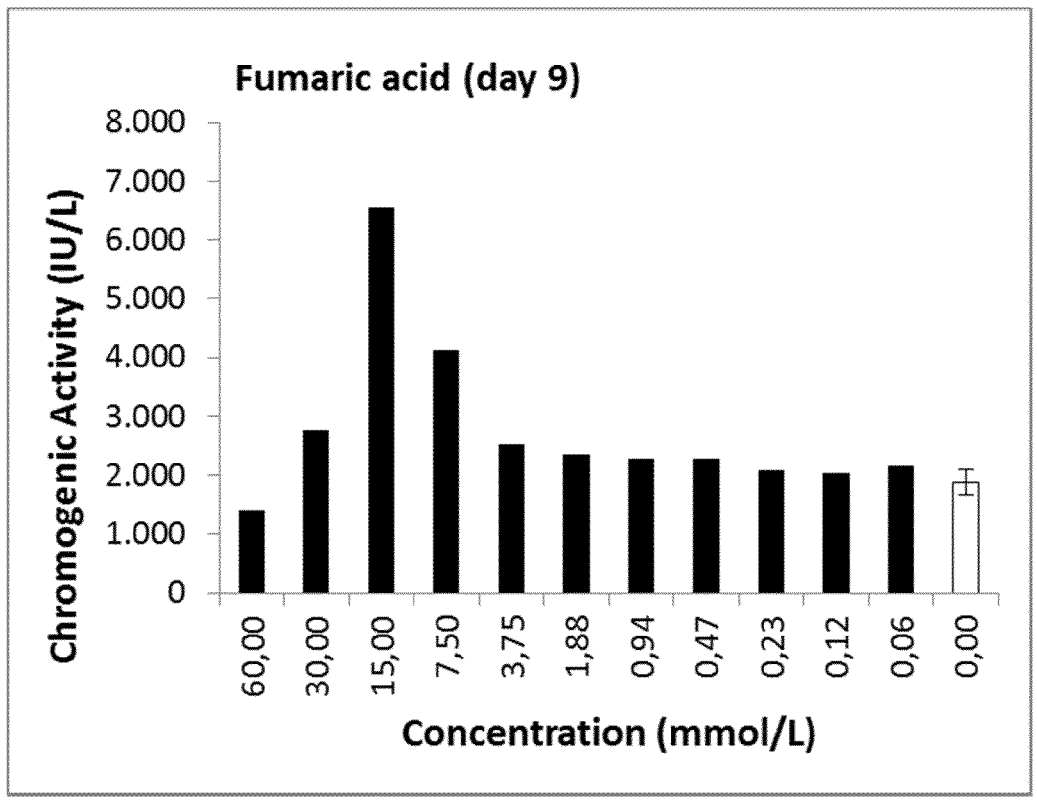
Figure 6C:
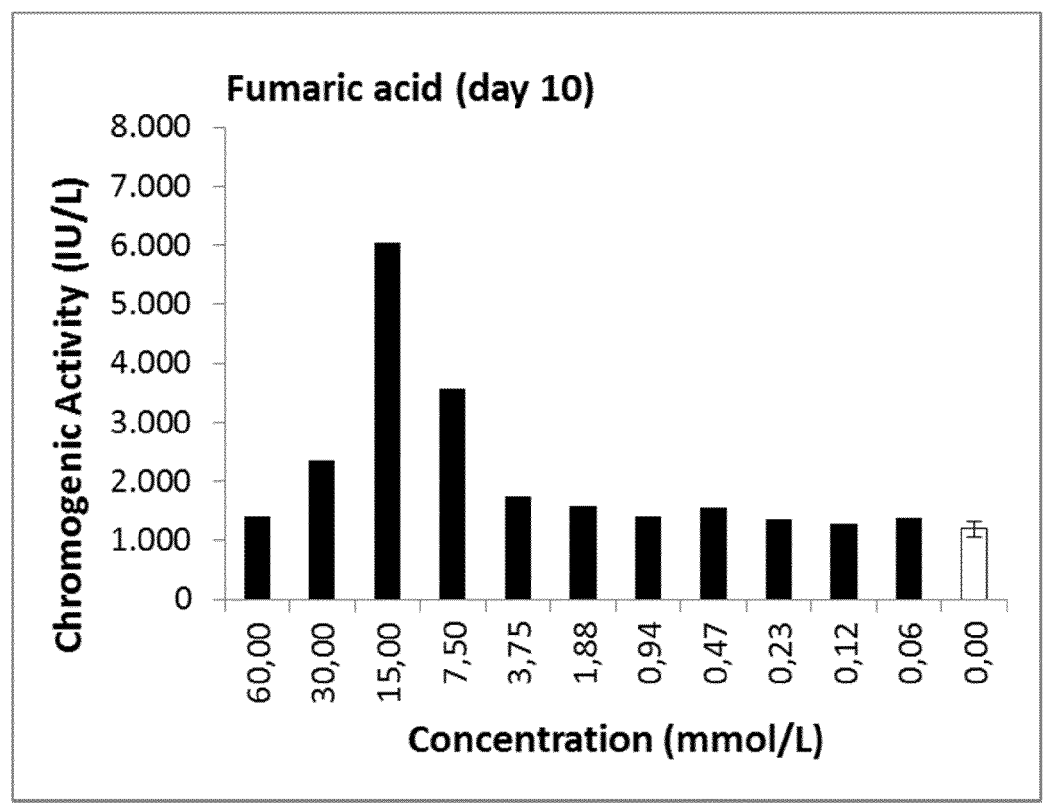
Figure 7A:
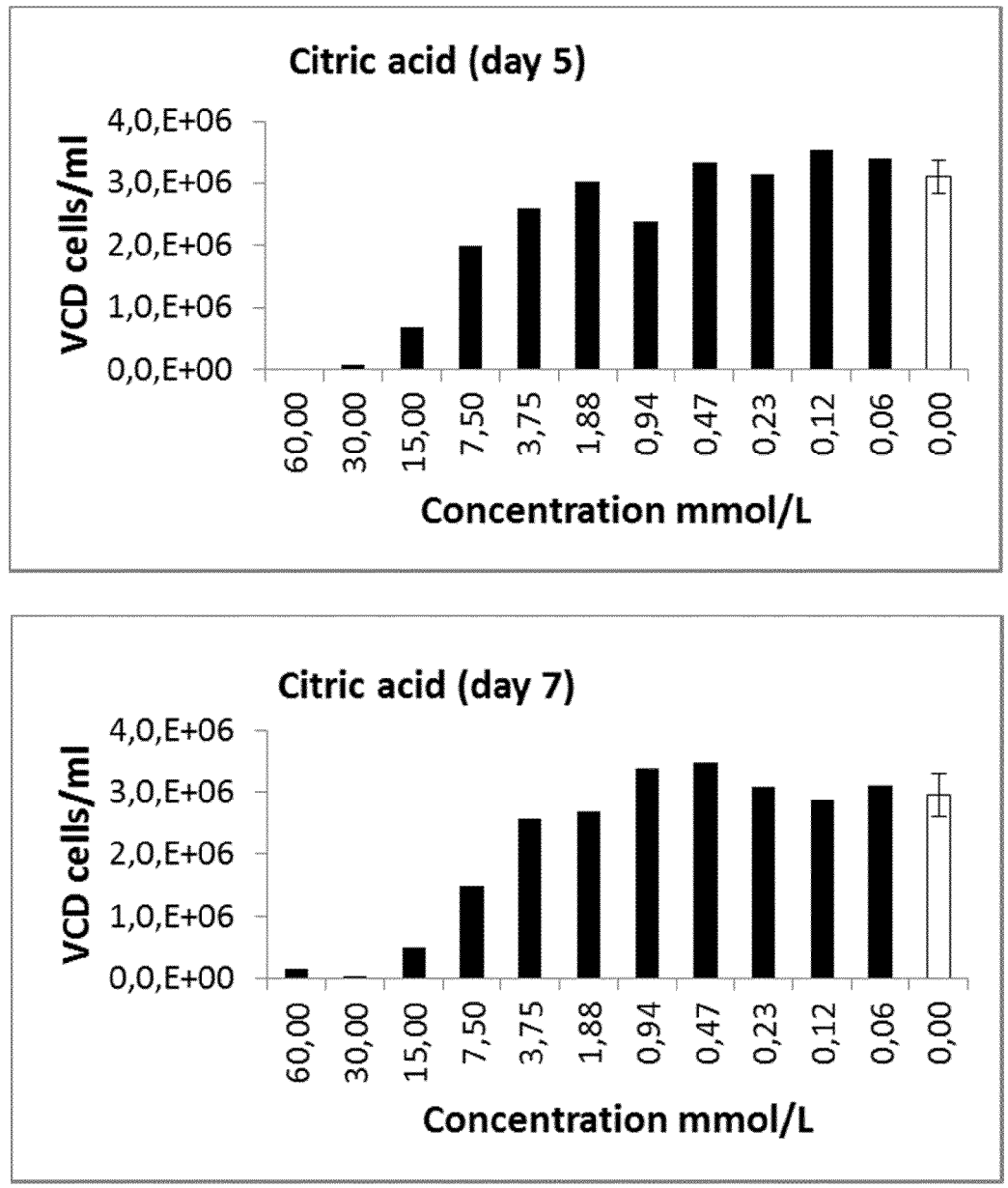
FIG. 7A: Viable cell density of CHO cells expressing FVII that are grown in the presence of different concentrations of citric acid for 5 or 7 days, respectively.
Figure 7B:
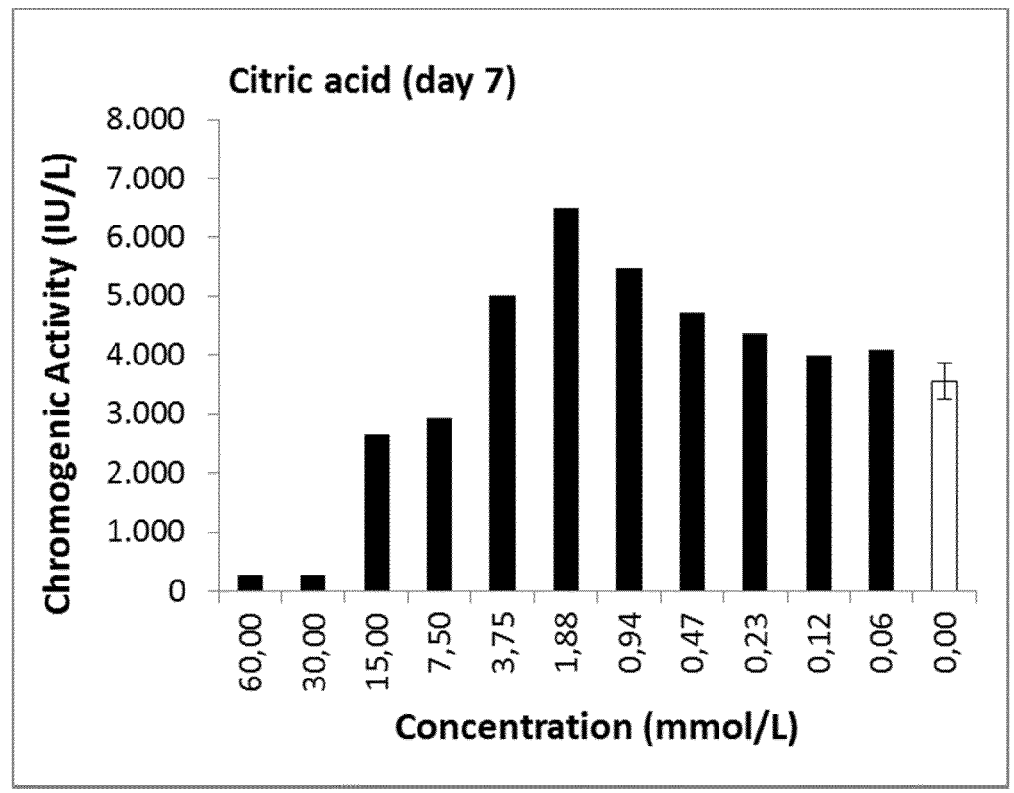
FIGS. 7B+C: Chromogenic activity of FVII obtained from CHO cells expressing FVII that are grown in the presence of different concentrations of citric acid for 7, 9 or 10 days, respectively.
Figure 7B:
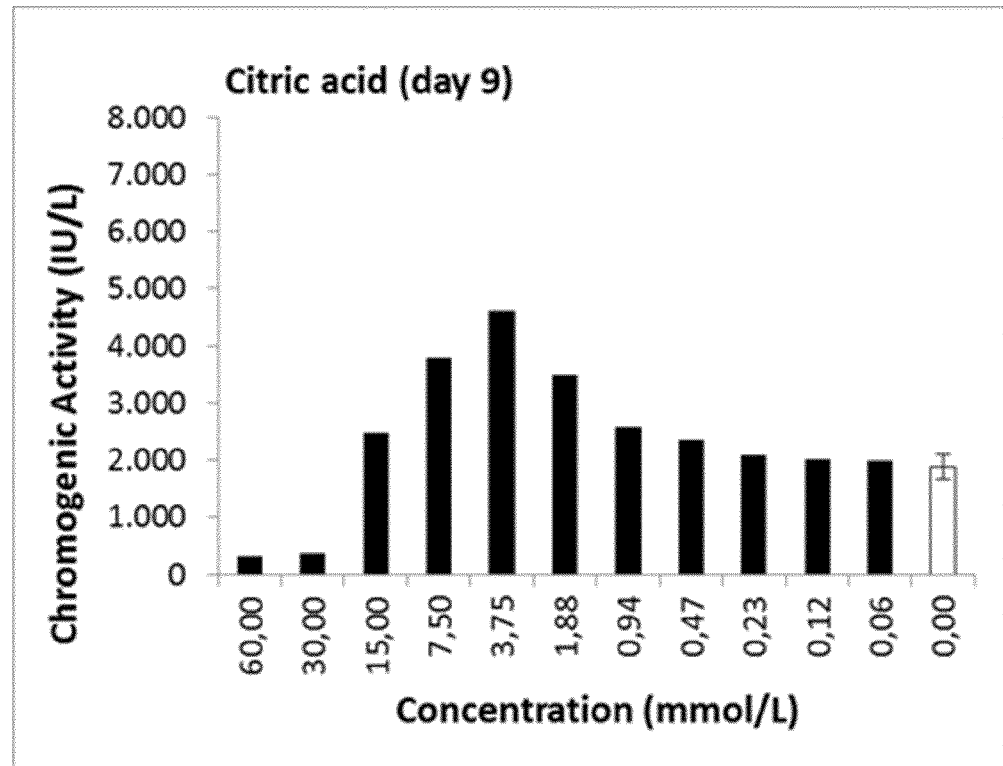
Figure 7C:
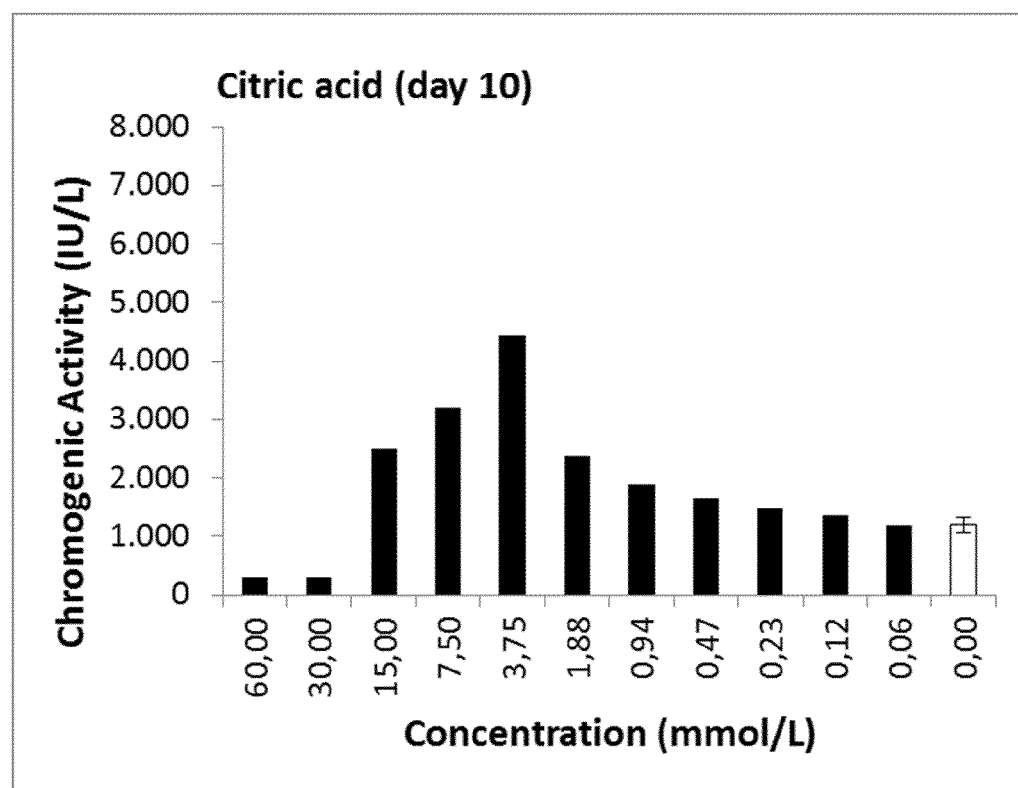

Recombinant Factor VII chromogenic activity in the cultures were determined from serially diluted supernatant samples obtained at days 7, 9 and 10 (counted from inoculation of the culture) using a commercially available chromogenic kit COASET Factor VII kit (Chromogenix). The assay was adapted for use with the SYSMEX® CS-5100 automated hemostasis analyzer (Siemens Healthcare) and performed according to manufacturers' instructions. Results are shown in FIGS. 1B and 1C. The results show that the presence of L-glutathione in the cell culture increases chromogenic activity of FVII.

Example 2

Cell Culture

Chinese Hamster Ovary cell line that expresses recombinant human Factor VII fusion protein was created using the GS expression system (Lonza). These cells were maintained in commercially available CD-CHO AGT medium (Invitrogen) supplemented with 50 μg/L reduced menadione sodium bisulfite (rMSB) (Richman), 25 μM methionine sulfoximine (MSX) (Sigma) and 1 mg/L insulin (Novo Nordisk). Cells were grown in shake flasks maintained at 37° C. with 8% CO2 atmosphere and subcultured every 3 days to 3×105 cells/mL.

Cells from the exponential growth phase of the cultures (at the end of regular 3-day passages) were used for the experiments. The cells were centrifuged, appropriate amount of spent media removed and cell pellets were resuspended in remaining spent media to a cell concentration of 3×106 cells/mL. 50 μL of this cell suspension was used to inoculate each well of a polypropylene V-bottom square 96-deepwell plate (Corning) containing 450 μL of a cell culture media based on DMEM/F12 supplemented with different levels of alpha-ketoglutaric acid (Sigma), malic acid (Sigma), succinic acid (Sigma), oxaloacetic acid (Sigma), fumaric acid (Sigma), citric acid (Sigma) or sodium pyruvate (Sigma). The alpha-ketoglutaric acid, malic acid, succinic acid, oxaloacetic acid, fumaric acid and citric acid concentration ranges tested were 0.06-60 mM with corresponding supplement-free negative controls. The sodium pyruvate concentration range tested was 0.01-10 mM with a corresponding supplement-free negative control. All cultures contained 213 μg/L rMSB to support appropriate cellular processing of Factor VII. All liquid handling steps were performed using a Tecan Freedom EVO® 200 robotic platform (Tecan).

Culture plates were sealed with a breathable membrane (Corning) to maintain sterility and cultures were maintained at 37° C. with 8% CO2 atmosphere in a shaker incubator (Kuhner) operating at 350 rpm with an oribital diameter of 25 mm.

Determination of Cell Growth and Viability

The cell density and viability were determined as described for Example 1. Results are shown in FIGS. 2A, 3A, 4A, 5A, 6A, 7A and 8A. The results show that at most concentrations tested, the indicated supplements have no effect on the viable cell density.

Quantification of Recombinant Factor VII

Recombinant Factor VII chromogenic activity in the cultures was determined as described for Example 1. Results are shown in FIGS. 2B, 2C, 3B, 3C, 4B, 4C, 5B, 5C, 6B, 6C, 7B, 7C, 8B and 8C. The results show that the presence of a TCA cycle intermediate in the cell culture increases chromogenic activity of FVII. Sodium pyruvate which was used as negative control has no effect on the chromogenic activity of FVII.

The invention claimed is:

1. A method comprising:
   culturing mammalian host cells that comprise an expression system for expressing a recombinant vitamin K-dependent protein under conditions suitable for achieving expression of the recombinant vitamin K-dependent protein in a cell culture medium comprising one or more cell culture enhancing reagent(s) at concentration(s) sufficient to enhance the activity of the recombinant vitamin K-dependent protein compared to a recombinant vitamin K-dependent protein expressed in mammalian host cells cultured in a cell culture medium lacking the cell culture enhancing reagent(s),
   wherein the one or more cell culture enhancing reagent(s) and concentration(s) is/are chosen from
   alpha-ketoglutaric acid at a concentration of 7.5-60 mmol/L,
   succinic acid at a concentration of 1.8-30 mmol/L,
   oxaloacetic acid at a concentration of 7.5-30 mmol/L,
   malic acid at a concentration of 7.5-30 mmol/L,
   fumaric acid at a concentration of 3.7-30 mmol/L, and
   citric acid at a concentration of 0.9-15 mmol/L.

2. The method of claim 1, wherein the cell culture medium comprises a combination of any two or more of alpha-ketoglutaric acid, succinic acid, oxaloacetic acid, malic acid, fumaric acid, and citric acid.

3. The method of claim 1, comprising providing the one or more cell culture enhancing reagent(s) at the beginning of the cell culturing.

4. The method of claim 1, wherein the cell culture is a fed-batch culture, and wherein the one or more cell culture enhancing reagent(s) is/are present in a basal cell culture medium and/or in a feed medium.

5. The method of claim 1, wherein the cell culture is a perfusion culture, and wherein the one or more cell culture enhancing reagent(s) is/are present in a basal cell culture medium and/or in a perfusion medium.

6. The method of claim 1, wherein the cell culture medium is free of any proteins from human or animal origin.

7. The method of claim 1, wherein the host cells are Chinese hamster ovary (CHO) cells.

8. The method of claim 1, wherein the recombinant vitamin K-dependent protein is selected from Factor IX (FIX), Factor VII (FVII), Factor X (FX), Factor II (FII), Protein C, Protein S, Protein Z, osteocalcin, the calcification inhibiting matrix Gla protein (MGP), and the cell growth regulating growth arrest specific protein 6 (Gas6).

9. The method of claim 1, wherein the recombinant vitamin K-dependent protein is a FVII protein.

10. The method of claim 1, wherein the recombinant vitamin K-dependent protein is a FVII fusion protein.

11. The method of claim 1, wherein the recombinant vitamin K-dependent protein is a FVII albumin fusion protein.

* * * * *